United States Patent [19]
Braun et al.

[11] Patent Number: 6,074,835
[45] Date of Patent: Jun. 13, 2000

[54] DIAGNOSIS, PREVENTION AND TREATMENT OF ULCERATIVE COLITIS, AND CLINICAL SUBTYPES THEREOF, USING HISTONE H1

[75] Inventors: Johnathan Braun, Tarzana; Stephan R. Targan, Santa Monica; Mark Eggena, Los Angeles, all of Calif.

[73] Assignees: Regents of the Univ. of California, Oakland; Cedars-Sinai Medical Center, Los Angeles, both of Calif.

[21] Appl. No.: 08/837,058

[22] Filed: Apr. 11, 1997

Related U.S. Application Data

[60] Provisional application No. 60/057,846, Apr. 12, 1996.

[51] Int. Cl.$^7$ .................................................. G01N 33/564
[52] U.S. Cl. ...................... 435/7.211; 435/7.24; 435/7.95; 436/506; 436/508
[58] Field of Search .................................. 435/7.21, 7.24, 435/7.85; 436/506, 508

[56] References Cited

U.S. PATENT DOCUMENTS 4,870,006  9/1989  Dragon et al. ........................... 435/7.22

OTHER PUBLICATIONS

Pool et al, GUT, 34, 46–50, 1993.
Proudjansky et al, J. Pediat. Gastruent. Nutr. 17, 193–197, 1993.
Reumaux et al, Clin. Immunol. Immunopath., 77, 349–357, 1995.
Saxon et al, J. Allerg. Clin. Immunol., 86, 202–210, 1990.
Sobajima et al, Clin. Exp. Immunol., 107, 135–140, 1997.
Bradbury, "Reversible Histone Modifications and the Chromosome Cell Cycle," *BioEssays* 14:9–16 (1992).
Doenecke et al., "Organization and Expression of H1 Histone and H1 Replacement Histone Genes," *J. Cell. Biochem.* 54:423–431 (1994).
Lu et al., "Generation and Characterization of Novel Antibodies Highly Selective for Phosphorylated Linker Histone H1 in Tetrahymena and HeLa Cells," *Chromosoma* 103:111–121 (1994).
Muller et al., "Immunogenicity of Free Histones and of Histones Complexed with RNA," *Molec. Immunol.* 28:763–772 (1991).
Parseghian et al., "Characterization of a Set of Antibodies Specific for Three Human Histone H1 Subtypes," *Chromosomam* 103:198–208 (1994).
Parseghian et al., "A Proposal for a Coherent Mammalian Histone H1 Nomenclature Correlated with Amino Acid Sequences," *Protein Sci.* 3:575–587 (1994).
Rubin and Farber (eds.), "Inflammatory Bowel Disease," *Pathology* (2nd Ed.), pp. 675–683 (1994).
Saxon et al., "A Distinct Subset of Antineutrophil Cytoplasmic Antibodies is Associated with Inflammatory Bowel Disease," *J. Allergy Clin. Imunol.* 86:202–210 (1990).
Steinman, "Escape from 'Horror Autotoxicus': Pathogenesis and Treatment of Autoimmune Disease," *Cell* 80:7–1 (1995).
Tan, "Autoantibodies in Pathology and Cell Biology," *Cell* 67:841–842 (1991).
Weiner et al., "Oral Tolerance: Immunologic Mechanisms and Treatment of Animal and Human Organ–Specific Autoimmune Diseases by Oral Administration of Autoantigens," *Ann. Rev. Immunol.* 12:809–837 (1994).
Weiner, "Oral Tolerance: Mobilizing the Gut," *Hosp. Prac.* 53–58 (Sep. 15, 1995).

*Primary Examiner*—David Saunders
*Attorney, Agent, or Firm*—Campbell & Flores LLP

[57] ABSTRACT

The present invention provides a method of diagnosing ulcerative colitis (UC) in a subject suspected of having inflammatory bowel disease by by obtaining a sample from the individual; contacting the sample with human histone H1, or pANCA-reactive fragment thereof, under conditions suitable to form a complex of human histone H1, or pANCA-reactive fragment thereof, and antibody to human histone H1; and detecting the presence or absence of the complex, where the presence of the complex indicates that the individual has UC. The invention also provides related methods of diagnosing a perinuclear anti-neutrophil cytoplasmic antibody positive (pANCA-positive) clinical subtype of UC in a patient with UC. In addition, the invention further provides methods of determining susceptibility to UC in an individual. The invention further provides methods of inducing tolerance in a pANCA-positive patient with UC by administering an effective dose of histone H1, or tolerogenic fragment thereof, to the pANCA-positive patient with UC. Compositions of histone H1, or fragment thereof, combined with a tolerogizing molecule also are provided.

21 Claims, 6 Drawing Sheets

Human Histone H1$^S$-1 (SEQ ID NO: 1)
SETAPAAPAAAPPAEKAPVKKKAAKKAGGTPRKASGPPVSELITKAVA
ASKERSGVSLAALKKALAAAGYDVEKNNSRIKLGLKSLVSKGTLVQTK
GTGASGSFKLNKKAASGEAKPKVKKAGGTKPKKPVGAAKKPKKAAG
GATPKKSAKKTPKKAKKPAAATVTKKVAKSPKKAKVAKPKKAAKSA
AKAVKPKAAKPKVVKPKKAAPKKK Human Histone H1$^S$-2 (SEQ ID NO: 2)
SETAPLAPTIPAPAEKTPVKKKAKKAGATAGKRKASGPPVSELITKAVA
ASKERSGVSLAALKKALAAAGYDVEKNNSRIKLGLKSLVSKGTLVQTK
GTGASGSFKLNKKAASGEGKPKAKKAGAAKPRKPAGAAKKPKKVAG
AATPKKSIKKTPKKVKKPATAAGTKKVAKSAKKVKTPQPKKAAKSPA
KAKAPKPKAAKPKSGKPKVTKAKKAAPKKK Human Histone H1$^S$-3 (SEQ ID NO: 3)
SETAPAETATPAPVEKSPAKKKATKKAAGAGAAKRKATGPPVSELITK
AVAASKERNGLSLAALKKALAAGGYDVEKNNSRIKLGLKSLVSKGTL
VQTKGTGASGSFKLNKKAASGEAKPKAKKAGAAKAKKPAGATPKKA
KKAAGAKKAVKKTPKKAKKPAAAGVKKVAKSPKKAKAAAKPKKAT
KSPAKPKAVKPKAAKPKAAKPKAAKPKAKKAAAKKK Human Histone H1$^S$-4 (SEQ ID NO: 4)
SETAPAAPAAPAPAEKTPVKKKARKSAGAAKRKASGPPVSELITKAVA
ASKERSGVSLAALKKALAAAGYDVEKNNSRIKLGLKSLVSKGTLVQTK
GTGASGSFKLNKKAASGEAKPKAKKAGAAKAKKPAGAAKKPKKATG
AATPKKSAKKTPKKAKKPAAAGAKKAKSPKKAKAAKPKKAPKSPA
KAKAVKPKAAKPKTAKPKAAKPKKAAAKKK Human Histone H1° (SEQ ID NO: 5)
TENSTSAPAAKPKRAKASKKSTDHPKYSDMIVAAIQAEKNRAGSSRQSI
QKYIKSHYKVGENADSQIKLSIKRLVTTGVLQTKGVGASGSFRLAKS
DEPKKSVAFKKTKKEIKKVATPKKASKPKKAASKAPTKKPKATPVKKA
KKKLAATPKKAKKPKTVKAKPVKASKPKKAKPVKPKAKSSAKRAGK
KK Human Histone H1t (SEQ ID NO: 6)
SETVPAASASASAGVAAMEKLPTKKRGRKPAGLISASRKVPNLSVSKLITE
ALSVSQERVGMSLVALKKALAAAGYDVEKNNSRIKLSLKSLVNKGILV
QTRGTGASGSFKLSKKVIPKSTRSKAKKSVSAKTKKLVLSRDSKSPKTA
KTNKRAKKPRATTPKTVRSGRKAKGAKGKQKQKSPVKARASKSKLTQ
HHEVNVRKATSKK

FIG. 1

NANUC-1

NANUC-2

TT 6,074,835

DIAGNOSIS, PREVENTION AND TREATMENT OF ULCERATIVE COLITIS, AND CLINICAL SUBTYPES THEREOF, USING HISTONE H1

RELATED APPLICATIONS

This application claims the benefit of U.S. Provisional Application No. 60/057,846, filed Apr. 12, 1996, which was converted from application Ser. No. 08/630,671 and which is incorporated herein by reference.

ACKNOWLEDGMENT

This work was supported by grant number DK46763 awarded by the National Institutes of Health and by grant number GM08042 awarded by the National Institutes of Health. The United States government has certain rights in this invention.

BACKGROUND OF THE INVENTION

1. Field of the Invention

The invention relates generally to the fields of autoimmunity and inflammatory bowel disease and more specifically to the diagnosis and treatment of a clinical subtype of ulcerative colitis.

2. Background Information

Inflammatory bowel disease (IBD) is the collective term used to describe two gastrointestinal disorders of unknown etiology: Crohn's disease (CD) and ulcerative colitis (UC). The course and prognosis of ulcerative colitis, which occurs world-wide and is reported to afflict as many as two million people, varies widely. Onset of ulcerative colitis is predominantly in young adulthood with diarrhea, abdominal pain, and fever the three most common presenting symptoms. The diarrhea may range from mild to severe and often is accompanied by bleeding. Anemia and weight loss are additional common signs of UC. Ten percent to fifteen percent of all patients with inflammatory bowel diseases such as UC will require surgery over a ten year period. In addition, patients with UC are at increased risk for the development of intestinal cancer. Reports of an increasing occurrence of psychological problems, including anxiety and depression, are perhaps not surprising symptoms of what is often a debilitating disease that strikes people in the prime of life.

Unfortunately, the available therapies for ulcerative colitis are few, and both diagnosis and treatment have been hampered by a lack of knowledge regarding the etiology of the disease. What is clear, however, is that the pathogenesis of ulcerative colitis involves immune-mediated damage to the intestinal mucosa. Autoantibodies, specifically antibodies against cytoplasmic components of neutrophils (pANCA), have been reported in 68–80% of patients with ulcerative colitis, further supporting a role for immune dysregulation in this disease. However, the UC pANCA target antigen, which would be useful in diagnosing and treating the large population of UC patients that have pANCA autoantibodies has, to date, escaped identification. Thus, there is a need for methods of diagnosing and treating ulcerative colitis using the ulcerative colitis pANCA target antigen. The present invention satisfies this need and provides related advantages as well.

SUMMARY OF THE INVENTION

The present invention provides methods of diagnosing ulcerative colitis (UC) by obtaining a sample from a subject suspected of having inflammatory bowel disease; contacting the sample with human histone H1, or pANCA-reactive fragment thereof, under conditions suitable to form a complex of human histone H1, or pANCA-reactive fragment thereof, and antibody to human histone H1; and detecting the presence or absence of the complex, where the presence of the complex indicates that the subject has ulcerative colitis. Human histone H1 useful in these methods can be, for example, histone H1 isoform H1$^S$-2 or a pANCA-reactive fragment thereof such as SEQ ID NO: 7, SEQ ID NO: 13, SEQ ID NO: 14 or SEQ ID NO: 20.

The invention also provides methods of diagnosing a perinuclear anti-neutrophil cytoplasmic antibody-positive (pANCA-positive) clinical subtype of ulcerative colitis (UC) in a patient with UC. A pANCA-positive clinical subtype of UC can be diagnosed, for example, by obtaining a sample from a patient with UC; contacting the sample with human histone H1, or pANCA-reactive fragment thereof, under conditions suitable to form a complex of human histone H1, or pANCA-reactive fragment thereof, and antibody to human histone H1; and detecting the presence or absence of the complex, where the presence of the complex indicates that the patient has the pANCA-positive clinical subtype of UC. For use in these methods, a useful human H1 histone is, for example, isoform H1$^S$-2, or a pANCA-reactive fragment thereof such as SEQ ID NO: 7, SEQ ID NO: 13, SEQ ID NO: 14 or SEQ ID NO: 20.

The invention also provides methods of determining susceptibility to UC in an individual by obtaining a sample from the individual; contacting the sample with human histone H1; or pANCA-reactive fragment thereof, under conditions suitable to form a complex of human histone H1, or pANCA-reactive fragment thereof, and antibody to human histone H1; and detecting the presence or absence of the complex, where the presence of the complex indicates that the individual has increased susceptibility to UC. Susceptibility to UC can be determined according to the methods of the invention using, for example, histone H1 isoform H1$^S$-2, or a pANCA-reactive fragment thereof such as SEQ ID NO: 7, SEQ ID NO: 13, SEQ ID NO: 14 or SEQ ID NO: 20.

Methods of inducing tolerance in a pANCA-positive patient with UC by administering to the patient an effective dose of histone H1, or tolerogenic fragment thereof, also are provided. A tolerogenic fragment of histone H1 that is particularly useful for inducing tolerance can be derived from histone H1 isoform H1$^S$-2 and can include, for example, the amino acid sequence Pro-Lys-Lys-Ala-Lys-Lys-Pro-Ala-Ala-Ala-Thr-Val-Thr-Lys-Lys (SEQ ID NO: 20). Additionally, histone H1, or a fragment thereof, can be combined with various molecules known to cause, promote or enhance tolerogenic activity.

Methods of preventing UC in an individual by administering to the individual an effective dose of histone H1, or tolerogenic fragment thereof, also are provided. Such methods are particularly useful for preventing UC in an individual having increased susceptibility to UC. A tolerogenic fragment of histone H1 that is particularly useful for preventing UC in an individual can be derived from histone H1 isoform H1$^S$-2 and can include, for example, the amino acid sequence SEQ ID NO: 20.

BRIEF DESCRIPTION OF THE DRAWINGS

FIG. 1 shows the amino acid sequences of human histone H1 isoforms H1$^S$-1, H1$^S$-2, H1$^S$-3, H1$^S$-4, H1$^o$ and H1t.

DETAILED DESCRIPTION OF THE INVENTION

Perinuclear anti-neutrophil cytoplasmic antibodies (pANCA) are present in the sera of most patients with ulcerative colitis (UC), and are a familial trait associated with disease susceptibility and disease-associated MHC haplotypes. Although sera from pANCA-positive ulcerative colitis patients is known to react with a component of neutrophils, the antigen responsible for the UC pANCA reactivity has long eluded identification. The present invention is directed to the exciting discovery that the pANCA autoantibody present in the sera of most patients with UC reacts with histone H1.

Figure 2:
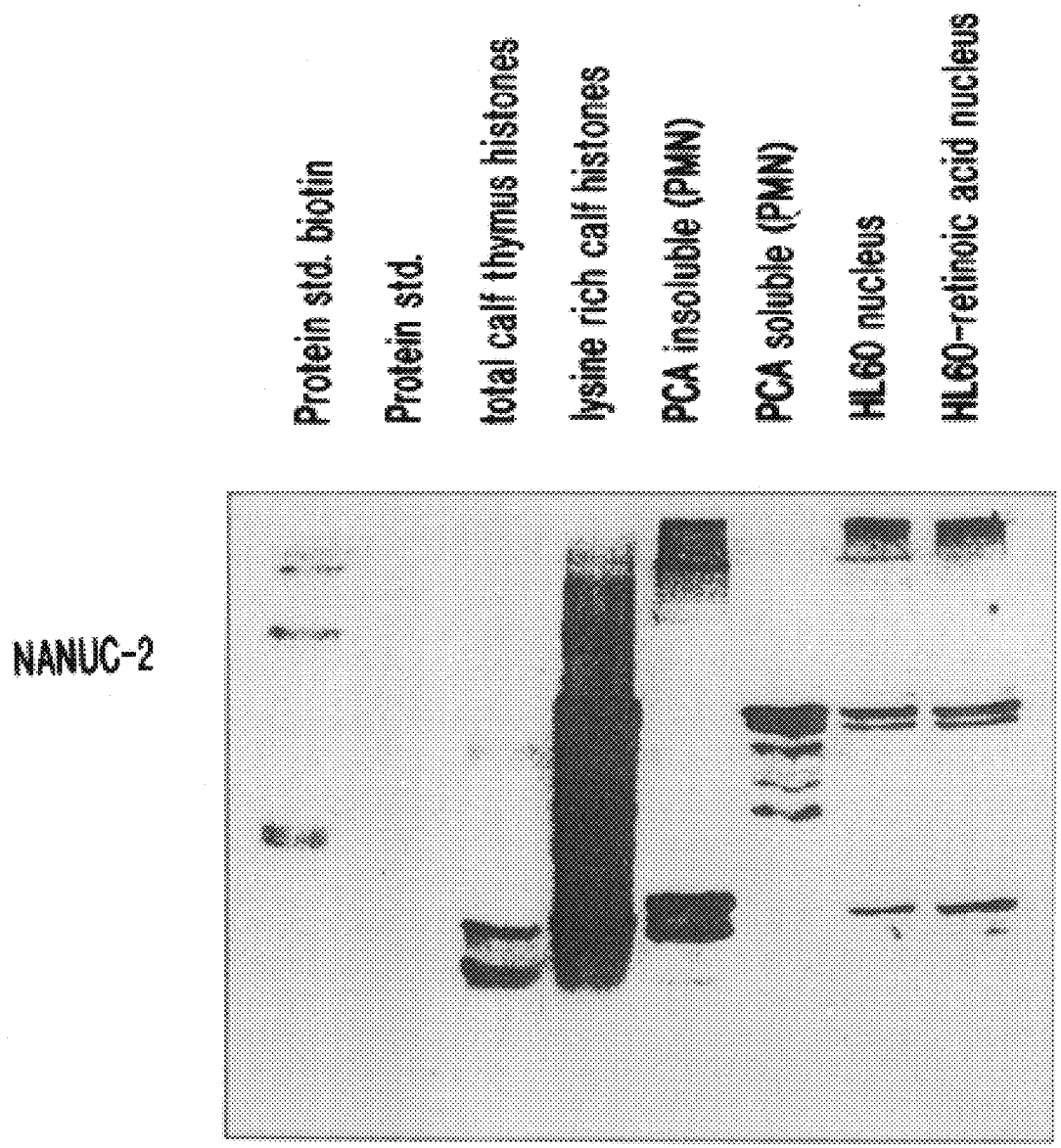
FIG. 2 shows Western analysis with a representative pANCA monoclonal, NANUC-2. Protein samples represent a HL60 cell nuclear fraction, purified calf thymus histones and histones purified from human neutrophils (PMN). The perchloric acid (PCA) insoluble PMN fraction contains the core histones, while the perchloric acid soluble fraction contains histone H1.
Figure 3A:
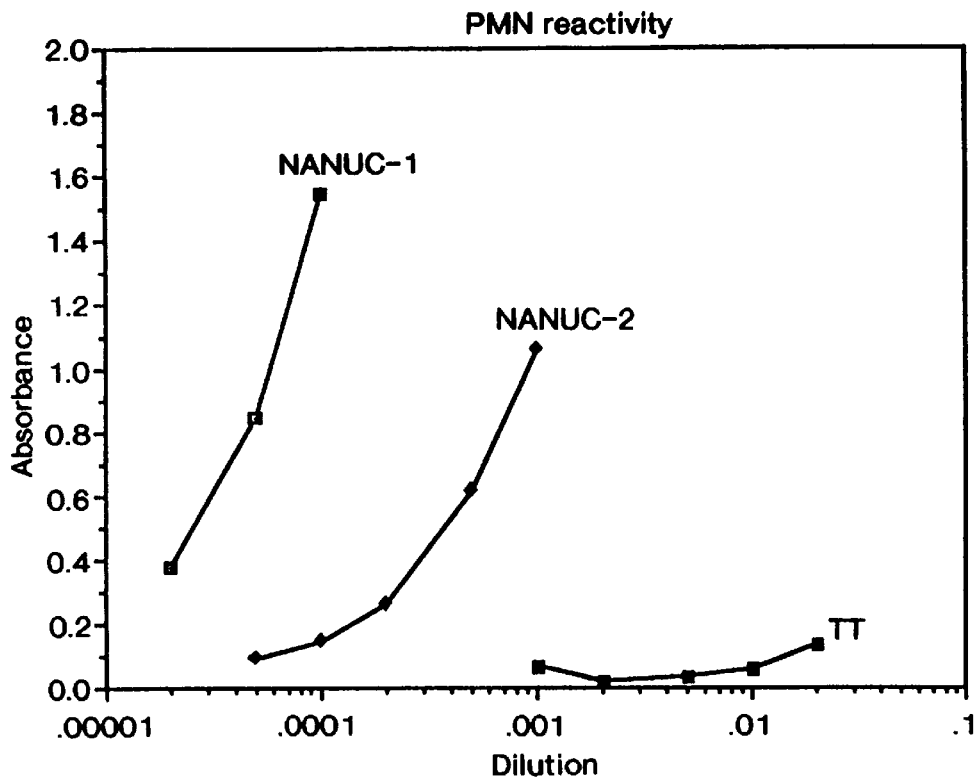
FIG. 3A shows enzyme-linked immunosorbent assay analysis of neutrophil (PMN) with NANUC-1, NANUC-2 or Anti-Tetanus Toxoid antibody (TT).
Figure 3B:
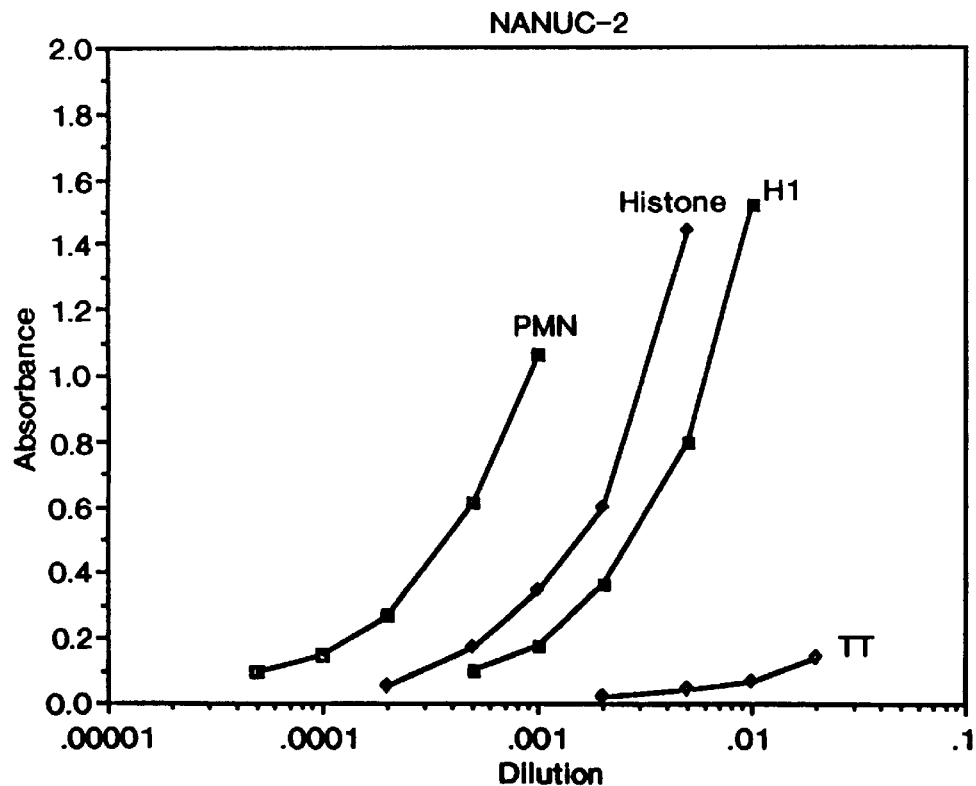
FIG. 3B shows enzyme-linked immunosorbent assay analysis of NANUC-1 with neutrophil (PMN), total calf thymus histones (histone), purified calf thymus histone H1 (H1) or tetanus toxoid antigen (TT).
Figure 3C:
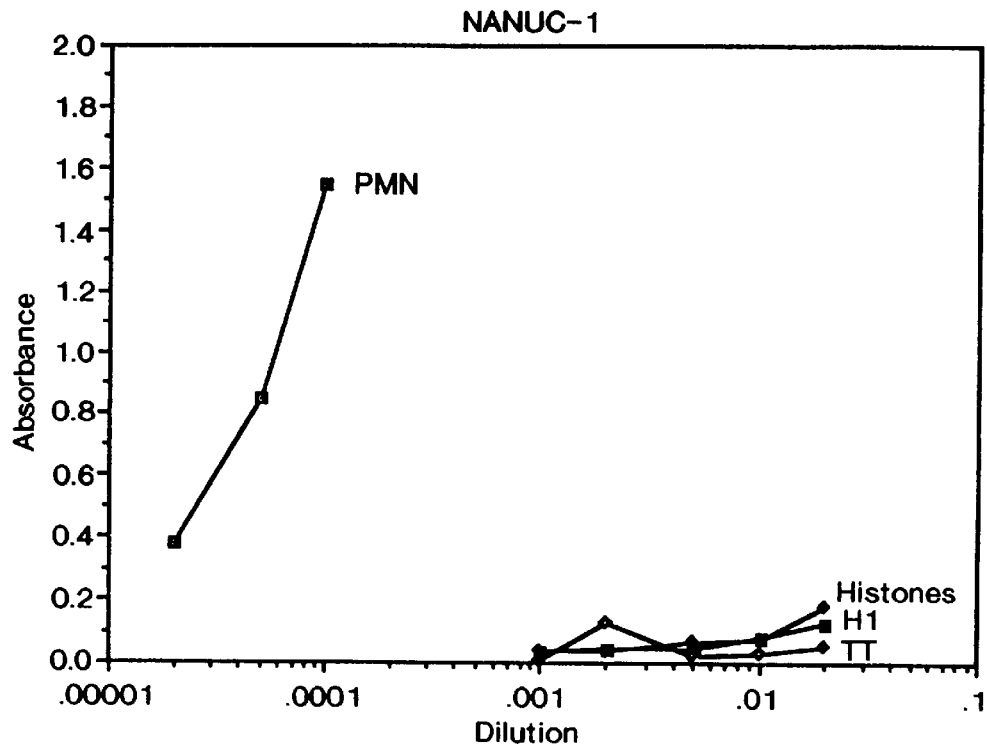
FIG. 3C shows enzyme-linked immunosorbent assay analysis of NANUC-2 with neutrophil (PMN), total calf thymus histones (histone), purified calf thymus histone H1 (H1) or tetanus toxoid antigen (TT).
Figure 3D:
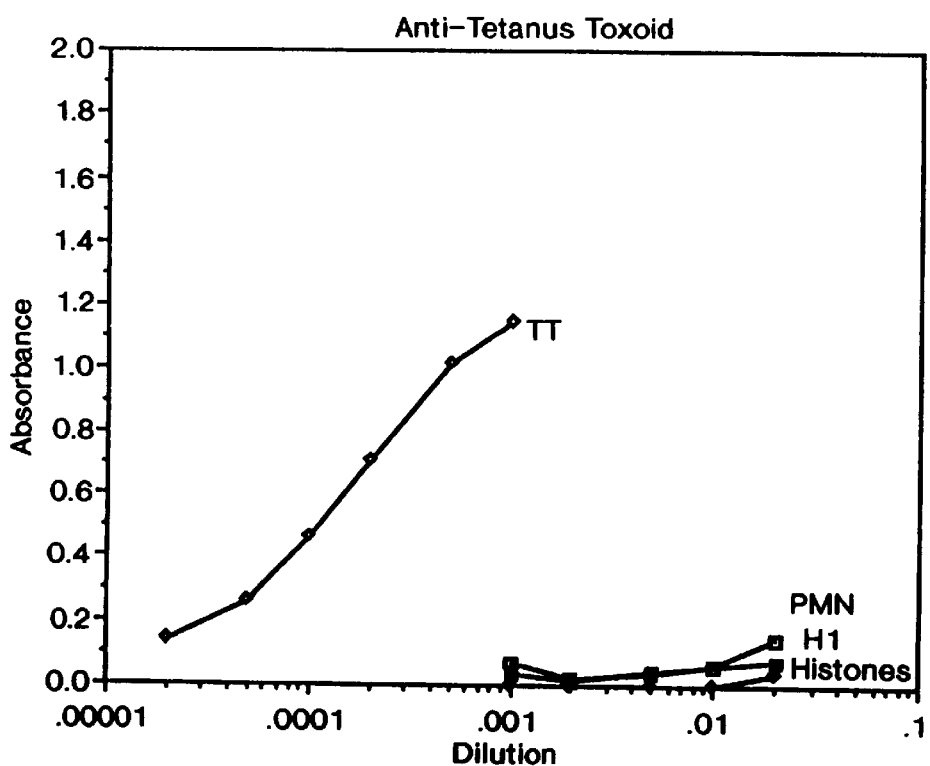
FIG. 3D shows enzyme-linked immunosorbent assay analysis of Anti-Tetanus Toxoid antibody with tetanus toxoid antigen (TT), neutrophil (PMN), purified calf thymus histone H1 (H1) or total calf thymus histones (histone).

As disclosed herein, Western analysis demonstrates that a nuclear protein doublet of 32–33 kDa from neutrophils is specifically reactive with a representative UC pANCA monoclonal antibody, NANUC-2 (see FIG. 2). Purification and protein sequencing of the NANUC-2 reactive protein doublet identified the UC pANCA target antigen as histone H1. Specific binding of NANUC-2 to histone H1 was confirmed using purified human neutrophil histone H1 and purified calf thymus histone H1. Identification of histone H1 as a UC pANCA target antigen provides a valuable reagent for diagnosing the presence of pANCA in UC patients and for ameliorating the abnormal immune process involved in ulcerative colitis. Thus, the invention is directed to methods for diagnosing a pANCA-positive clinical subtype of UC and determining susceptibility to UC using histone H1. The invention also is directed to methods of treating UC by inducing tolerance in a pANCA-positive UC patient and preventing UC in a healthy individual by administering the recently identified UC pANCA target antigen, histone H1.

The present invention provides methods of diagnosing ulcerative colitis (UC) by obtaining a sample from a subject suspected of having inflammatory bowel disease; contacting the sample with human histone H1, or pANCA-reactive fragment thereof, under conditions suitable to form a complex of human histone H1, or pANCA-reactive fragment thereof, and antibody to human histone H1; and detecting the presence or absence of the complex, where the presence of the complex indicates that the subject has ulcerative colitis. Human histone H1 useful in these methods can be, for example, histone H1 isoform H1$^S$-2 or a pANCA-reactive fragment thereof such as SEQ ID NO: 7, SEQ ID NO: 13, SEQ ID NO: 14 or SEQ ID NO: 20.

The present invention also provides methods of diagnosing a pANCA-positive clinical subtype of ulcerative colitis in a patient with UC. A pANCA-positive clinical subtype of UC can be diagnosed, for example, by obtaining a sample from a patient with UC; contacting the sample with human histone H1, or pANCA-reactive fragment thereof, under conditions suitable to form a complex of human histone H1, or pANCA-reactive fragment thereof, and antibody to human histone H1; and detecting the presence or absence of the complex, where the presence of the complex indicates that the patient has the pANCA-positive clinical subtype of UC. A pANCA-positive clinical subtype of UC also can be diagnosed by obtaining a sample from a patient with UC; contacting the sample with purified histone H1 isoform H1$^S$-2, or pANCA-reactive fragment thereof, under conditions suitable to form a complex of histone H1 isoform H1$^S$-2, or pANCA-reactive fragment thereof, and antibody to histone H1 isoform H1$^S$-2; and detecting the presence or absence of the complex, where the presence of the complex indicates that the patient has the pANCA-positive clinical subtype of UC.

The methods of the invention relate to diagnosing and treating ulcerative colitis (UC), which is a disease of the large intestine characterized by chronic diarrhea with cramping abdominal pain, rectal bleeding, and loose discharges of blood, pus and mucus. The manifestations of this disease vary widely. A pattern of exacerbations and remissions typifies the clinical course of most UC patients (70%), although continuous symptoms without remission are present in some patients with UC. Local and systemic complications of UC include arthritis, eye inflammation such as uveitis, skin ulcers and liver disease. In addition, ulcerative colitis and especially long-standing, extensive disease is associated with an increased risk of colon carcinoma.

Several pathologic features characterize UC in distinction to other inflammatory bowel diseases. Ulcerative colitis is a diffuse disease that usually extends from the most distal part of the rectum for a variable distance proximally. The term left-sided colitis describes an inflammation that involves the distal portion of the colon, extending as far as the splenic flexure. Sparing of the rectum or involvement of the right side (proximal portion) of the colon alone is unusual in ulcerative colitis. Furthermore, the inflammatory process of UC is limited to the colon and does not involve, for example, the small intestine, stomach or esophagus. In addition, ulcerative colitis is distinguished by a superficial inflammation of the mucosa that generally spares the deeper layers of the bowel wall. Crypt abscesses, in which degenerate intestinal crypts are filled with neutrophils, also are typical of the pathology of ulcerative colitis (Rubin and Farber, *Pathology* (Second Edition) Philadelphia: J.B. Lippincott Company (1994), which is incorporated herein by reference).

As used herein, the term "ulcerative colitis" is synonymous with "UC" and means a disease having clinical features of left-sided colonic disease accompanied by a characteristic endoscopic or histopathologic feature of UC. Clinical features of left-sided colonic disease, as used herein, are rectal bleeding, urgency and tenesmus. The rectal bleeding may be accompanied by mucus discharge. Additional clinical features that may be present in UC include treatment with topical therapy and recommended or performed total or near-total colectomy.

A characteristic endoscopic feature of UC, which when present with clinical features of left-sided colonic disease indicates ulcerative colitis, is inflammation that is more severe distally than proximally or continuous inflammation. Additional typical endoscopic features that may be present in UC include inflammation extending proximally from the rectum or shallow ulcerations or the lack of deep ulcerations.

A characteristic histopathologic feature of UC, which when present with clinical features of left-sided colonic disease indicates ulcerative colitis, is homogeneous, continuous, predominantly superficial inflammation or a lack of "focality" within biopsy specimens. Additional typical histopathologic features that may be present in UC include the presence of crypt abscesses or a lack of granulomas. Characteristic clinical features of left-sided colonic disease and characteristic endoscopic and histopathologic features of ulcerative colitis are summarized in Table 1.

As used herein, the term "subject suspected of having inflammatory bowel disease" means any animal capable of having ulcerative colitis, including a human, non-human primate, rabbit, rat or mouse, especially a human, and having one or more symptoms of ulcerative colitis or Crohn's disease as described hereinabove.

As used herein, the term "patient with UC" means a patient having ulcerative colitis, as defined by the presence of clinical features of left-sided colonic disease accompanied by a characteristic endoscopic or histopathologic feature of UC as defined herein.

The pathogenesis of ulcerative colitis, although poorly understood, ultimately involves immune-mediated tissue damage. Ulcerative colitis is associated with various immunologic abnormalities, many of which can be secondary to inflammation. Similar to autoimmune disorders such as diabetes mellitus and multiple sclerosis, ulcerative colitis can represent a process of immune dysfunction directed against intrinsic intestinal mucosa cells. However, ulcerative colitis occurs in a mucosal site interfacing with the intestinal lumen. Thus, a primary immune target also can be an extrinsic agent such as a chronic microbial colonist. In this case, the mucosal injury characteristic of UC is a consequence of inflammatory bystander damage to resident parenchymal cells.

Host genetic factors can confer susceptibility or resistance to tissue damage elicited by a chronic local immune response. For example, IBD

TABLE 1

| | |
|---|---|
| A. Clinical features of left-sided colonic disease | 1. Rectal bleeding possibly accompanied by mucus discharge |
| | 2. Urgency |
| | 3. Tenesmus |
| | 4. Treatment with topical therapy |
| | 5. Recommended or performed total or near-total colectomy |
| B. Endoscopic features of UC | 6. Inflammation that is more severe distally than proximally |
| | 7. Continuous inflammation |
| | 8. Inflammation extending proximally from the rectum |
| | 9. Shallow ulcerations or lack of deep ulcerations |
| C. Histopathologic features of UC | 10. Homogeneous, continuous, predominantly superficial inflammation |
| | 11. Lack of "focality" within biopsy specimens |
| | 12. Crypt abscesses |
| | 13. Lack of granulomas | is associated with polymorphisms in MHC class II, ICAM-1 and TNF-$\alpha$ loci (Yang et al., *J. Clin. Invest.* 92:1080–1084 (1993)), and animal and clinical studies directly implicate TNF levels in disease. In the case of autoimmune diseases where the primary target is a self-antigen, host genetic factors can play a role in disease by controlling, for example, T-cell clonal abundance, peptide antigen presentation, and levels of cytokines modulating different effector responses. Host genetic diversity also can affect variable susceptibility to microbial organisms. Thus, pathogenesis of ulcerative colitis can result from a primary abnormality of the immune system, or from an initial injury by an infectious agent that is perpetuated through immune-mediated or other processes.

Certain immune-mediated disorders, including systemic lupus erythematosis, primary biliary cirrhosis and autoimmune hepatitis, are closely associated with distinctive patterns of autoantibody production. In the case of ulcerative colitis, anti-neutrophil cytoplasmic antibodies that produce a perinuclear staining pattern (pANCA) are elevated in 68–80% of UC patients and less frequently in other disorders of the colon. Serum titers of ANCA are elevated regardless of clinical status and, thus, do not reflect disease activity. High levels of serum ANCA also persist in patients five years post-colectomy. Although pANCA is found only very rarely in healthy adults and children, healthy relatives of UC patients have an increased frequency of pANCA, indicating that pANCA may be an immunogenetic susceptibility marker.

Serum antibodies to cytoplasmic components of a neutrophil (ANCA) can be detected, for example, using indirect immunofluorescence microscopy of alcohol-fixed neutrophils. ANCA activity has been divided into two broad categories: cytoplasmic neutrophil staining (cANCA) and perinuclear to nuclear staining or cytoplasmic staining with perinuclear highlighting (pANCA). As used herein, the term "perinuclear anti-neutrophil cytoplasmic antibody" is synonymous with "pANCA" and means an antibody that reacts specifically with a neutrophil to give perinuclear to nuclear staining or cytoplasmic staining with perinuclear highlighting.

The term "clinical subtype of UC," as used herein, means a subgroup of patients having ulcerative colitis whose features of disease are more similar to each other than to other patients with ulcerative colitis. The term "pANCA-positive clinical subtype of UC" means that subgroup of UC patients having pANCA.

Serum anti-neutrophil cytoplasmic antibodies previously have been used to characterize clinically distinct subsets of UC patients. For example, the presence of pANCA has been associated with treatment-resistant left-sided ulcerative colitis; aggressive UC (Vecchi et al., *Digestion* 55:34–39 (1994)); the requirement for surgery early in the course of UC (Boerr et al., *Gastroenterol.* 108: A785 (1995)) or development of pouchitis following ileal pouch-anal anastomosis for UC (Sandborn et al., *Gastroenterol.* 104: A774 (1993); Patel et al., *Br. J. Surg.* 81:724–726 (1994); Vecchi et al., *Lancet* 344:886–887 (1994); Sandborn et al., *Am. J. Gastroenterol.* 90:740–747 (1995)). Thus, the ability to identify a pANCA-positive clinical subtype of UC can be useful in predicting, for example, treatment-resistant UC; the progression of UC; the need for early surgery or the development of pouchitis.

The present invention is directed to the surprising discovery that an antigen that reacts with pANCA of ulcerative colitis is histone H1. Thus, the UC pANCA target antigen is a member of the histone family, which are highly-conserved proteins characterized by basic residues that contact the negatively charged phosphate groups in DNA and organize the DNA of eukaryotes into chromatin. Histones H2A, H2B, H3 and H4 are the core histones that make up nucleosomes, while histone H1, which is associated with nucleosomes at a 1 to 1 ratio, is required for higher order chromatin structure.

Histone H1 has a conserved central globular domain with extended, flexible N- and C-terminal domains. Sites of reversible chemical modification, such as phosphorylation and acetylation, occur in these extended N- and C-terminal regions and can regulate histone-DNA interactions (Bradbury et al.,*Bioessays* 14: 9–16 (1992)). The histone H1 family has multiple isoforms including $H1^S$-1, $H1^S$-2, $H1^S$-3 and $H1^S$-4, which are present in all normal somatic cells; the highly variable $H1^o$ isoform, which is associated with differentiated cell types; and the testis-specific isoform H1t (Parseghian et al., *Protein Sci.* 3:575–587 (1994), which is incorporated herein by reference). That functional differences can be associated with alternative histone H1 isoforms is supported by differences among the isoforms in the time of protein synthesis; turnover rate; amount and pattern of phosphorylation and ability to condense DNA in vitro.

As used herein, the term "histone H1" means one or more proteins having at least about 80% amino acid identity with at least one amino acid sequence of human histone H1 isoform $H1^S$-1 (SEQ ID NO: 1); $H1^S$-2 (SEQ ID NO: 2); $H1^S$-3 (SEQ ID NO: 3); $H1^S$-4 (SEQ ID NO: 4); $H1^o$ (SEQ ID NO: 5); or H1t (SEQ ID NO: 6). Thus, the term histone H1 encompasses, for example, one or more of the human histone H1 isoforms having an amino acid sequence shown in FIG. 1.

The term histone H1 also encompasses one or more non-human histone H1 isoforms having at least about 80% amino acid identity with at least one of the human histone H1 isoforms having an amino acid sequence shown in FIG. 1. For example, the term histone H1 encompasses, for example, a mouse or bovine $H1^S$-1 isoform having an amino acid sequence described in Parseghian et al., supra, 1994, or a rabbit or bovine $H1^S$-2 isoform having an amino acid sequence described in Parseghian et al., supra, 1994. Similarly, the term histone H1 encompasses, for example, a rabbit or rat $H1^S$-3 isoform having an amino acid sequence described in Parseghian et al., supra, 1994, or a mouse, rat, rabbit or bovine $H1^S$-4 isoform having an amino acid sequence described in Parseghian et al., supra, 1994. As disclosed herein, histone H1 useful in the invention can be obtained from a variety of species. For example, histone H1 that forms a complex with a representative UC monoclonal antibody (NANUC-2) and, thus, can form a complex with pANCA, can be purified from human neutrophil or calf thymus as described in Example I.

As used herein, the term "human histone H1" means one or more proteins having at least one amino acid sequence of human histone H1 isoform $H1^S$-1 (SEQ ID NO: 1); $H1^S$-2 (SEQ ID NO: 2); $H1^S$-3 (SEQ ID NO: 3); $H1^S$-4 (SEQ ID NO: 4); $H1^o$(SEQ ID NO: 5) or H1t (SEQ ID NO: 6).

As used herein, the term "histone H1 isoform $H1^S$-3" is synonymous with "$H1^S$-3" and means a protein having at least about 80% amino acid identity with the amino acid sequence of human histone isoform $H1^S$-3 (SEQ ID NO: 3) shown in FIG. 1. For example, the term $H1^S$-3 encompasses human histone H1 isoform $H1^S$-3 having the amino acid sequence (SEQ ID NO: 3) shown in FIG. 1. The term $H1^S$-3 also encompasses a non-human $H1^S$-3 protein having at least about 80% amino acid identity with the amino acid sequence shown as SEQ ID NO: 3, such as a rabbit or rat $H1^S$-3 isoform having an amino acid sequence described in Parseghian et al., supra, 1994.

As used herein, the term "histone H1 isoform $H1^S$-2" is synonymous with "$H1^S$-2" and means a protein having at least about 80% amino acid identity with the amino acid sequence of human histone isoform $H1^S$-2 (SEQ ID NO: 2) shown in FIG. 1. For example, the term $H1^S$-2 encompasses human histone H1 isoform $H1^S$-2 having the amino acid sequence (SEQ ID NO: 2) shown in FIG. 1. The term $H1^S$-2 also encompasses a non-human $H1^S$-2 protein having at least about 80% amino acid identity with the amino acid sequence shown as SEQ ID NO: 2, such as a rat or bovine $H1^S$-2 isoform having an amino acid sequence described in Parseghian et al., supra, 1994.

A sample useful in the methods of the invention can be obtained from any biological fluid having pANCA such as, for example, whole blood, plasma or other bodily fluid or tissue having pANCA, preferably serum. As used herein, the term "patient" means any animal capable of producing pANCA, including, for example, a human, non-human primate, rabbit, rat or mouse. A sample to be assayed according to the methods of the invention can be obtained from any such patient.

As used herein, the term "complex" is synonymous with "immune complex" and means an aggregate of two or more molecules that results from specific binding between an antigen, such as a protein or peptide, and an antibody. For example, a complex can be formed by specific binding of histone H1 to an antibody against histone H1.

As used herein, the term "antibody" means a population of immunoglobulin molecules, which can be polyclonal or monoclonal and of any isotype. As used herein, the term antibody encompasses an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

As used herein, the term "secondary antibody" means an antibody or combination of antibodies, which binds pANCA of UC. Preferably, a secondary antibody does not compete with histone H1 for binding to pANCA. A secondary antibody can be an anti-pANCA antibody that binds any epitope of pANCA. A particularly useful secondary antibody is an anti-IgG antibody having specificity for the class determining portion of pANCA. A useful secondary antibody is specific for the species of the ANCA to be detected. For example, if human serum is the sample to be assayed, mouse anti-human IgG can be a useful secondary antibody. A combination of different antibodies, which can be useful in the methods of the invention, also is encompassed within the meaning of the term secondary antibody, provided that at least one antibody of the combination binds pANCA of UC.

As used herein, the term "class determining portion," when used in reference to a secondary antibody, means the heavy chain constant-region sequence of an antibody that determines the isotype, such as IgA, IgD, IgE, IgG or IgM. Thus, a secondary antibody that has specificity for the class determining portion of an IgG molecule, for example, binds IgG in preference to other antibody isotypes.

A secondary antibody useful in the invention can be obtained commercially or by techniques well known in the art. Such an antibody can be a polyclonal or, preferably, monoclonal antibody that binds pANCA. For example, IgG reactive polyclonal antibodies can be prepared using IgG or Fc fragments of IgG as an immunogen to stimulate the production of antibodies in the antisera of an animal such as a rabbit, goat, sheep or rodent, as described in Harlow and Lane, *Antibodies: A Laboratory Manual* New York: Cold Spring Harbor Laboratory (1988), which is incorporated herein by reference.

A monoclonal antibody also is useful in the practice of the invention. As used herein, a monoclonal antibody refers to a population of antibody molecules that contain only one species of idiotope capable of binding a particular antigen epitope. Methods of producing a monoclonal antibody are well known (see, for example, Harlow and Lane, supra, 1988). An immunogen useful in generating a monoclonal antibody that binds pANCA can be, for example, human IgG or a Fc fragment of human IgG, pANCA or a Fab fragment of pANCA. A hybridoma that produces a useful monoclonal antibody can be identified by screening hybridoma supernatants for the presence of antibodies that bind pANCA (Harlow, supra, 1988). For example, hybridoma supernatants can be screened using neutrophil and pANCA-positive sera in a radioimmunoassay or enzyme-linked immunosorbent assay. In addition, a monoclonal antibody useful in the invention can be obtained from a number of commercial sources.

The term "detectable secondary antibody" means a secondary antibody, as defined above, that can be detected or measured by analytical methods. Thus, the term secondary antibody includes an antibody labeled directly or indirectly with a detectable marker that can be detected or measured and used in a convenient assay such as an enzyme-linked immunosorbent assay, radioimmunoassay, radial immunodiffusion assay or Western blotting assay, for example. A secondary antibody can be labeled, for example, with an enzyme, radioisotope, fluorochrome or chemiluminescent marker. In addition, a secondary antibody can be rendered detectable using a biotin-avidin linkage such that a detectable marker is associated with the secondary antibody. Labeling of the secondary antibody, however, should not impair binding of the secondary antibody to pANCA of UC. If desired, a multiple antibody system can be used as the secondary antibody as discussed above. In such a system, at least one of the antibodies is capable of binding pANCA of UC and at least one of the antibodies can be readily detected or measured by analytical methods.

A secondary antibody can be rendered detectable by labeling with an enzyme such as horseradish peroxidase (HRP), alkaline phosphatase (AP), β-galactosidase or urease, for example. A horseradish-peroxidase detection system can be used, for example, with the chromogenic substrate tetramethylbenzidine (TMB), which yields a soluble product in the presence of hydrogen peroxide that is detectable by measuring absorbance at 450 nm. An alkaline phosphatase detection system can be used with the chromogenic substrate p-nitrophenyl phosphate, for example, which yields a soluble product readily detectable by measuring absorbance at 405 nm. Similarly, a β-galactosidase detection system can be used with the chromogenic substrate o-nitrophenyl-β-D-galactopyranoside (ONPG), which yields a soluble product detectable by measuring absorbance at 410 nm, or a urease detection system can be used with a substrate such as urea-bromocresol purple (Sigma Immunochemicals, St. Louis, Mo.). A secondary antibody can be linked to an enzyme by methods well known in the art (Harlow and Lane, supra, 1988) or can be obtained from a number of commercial sources. For example, goat F(ab')2 anti-human IgG-alkaline phosphatase is a useful detectable secondary antibody that can be purchased from Jackson Immuno-Research (West Grove, Pa.).

A secondary antibody also can be rendered detectable by labeling with a fluorochrome. Such a fluorochrome emits light of ultraviolet or visible wavelength after excitation by light or another energy source. DAPI, fluorescein, Hoechst 33258, R-phycocyanin, B-phycoerythrin, R-phycoerythrin, rhodamine, Texas red or lissamine, for example, is a fluorochrome that can be linked to a secondary antibody and used to detect the presence or absence of a complex. A particularly useful fluorochrome is fluorescein or rhodamine. Methods of conjugating and using these and other suitable fluorochromes are described, for example, in Van Vunakis and Langone, *Methods in Enzymology*, Volume 74, Part C (1991), which is incorporated herein by reference. A secondary antibody linked to a fluorochrome also can be obtained from commercial sources. For example, goat F(ab')2 anti-human IgG-FITC is available from Tago Immunologicals (Burlingame, Calif.).

A pANCA titer also can be determined using a secondary antibody labeled with a chemiluminescent marker. Such a chemiluminescent secondary antibody is convenient for sensitive, non-radioactive detection of pANCA and can be obtained commercially from various sources such as Amersham Lifesciences, Inc. (Arlington Heights, Ill.).

A secondary antibody further can be rendered detectable by labeling with a radioisotope. An iodine-125 labeled secondary antibody is a particularly useful detectable secondary antibody (see, for example, Harlow and Lane, supra, 1988).

A signal from a detectable secondary antibody can be analyzed, for example, using a spectrophotometer to detect color from a chromogenic substrate; a fluorometer to detect fluorescence in the presence of light of a certain wavelength; or a radiation counter to detect radiation, such as a gamma counter for detection of iodine-125. For detection of an enzyme-linked secondary antibody, for example, a quantitative analysis of the amount of ANCA can be made using a spectrophotometer such as an EMAX Microplate Reader (Molecular Devices, Menlo Park, Calif.) in accordance with the manufacturer's instructions. If desired, the assays of the invention can be automated or performed robotically, and the signal from multiple samples can be detected simultaneously.

The assays of the present invention can be forward, reverse or simultaneous as described in U.S. Pat. No. 4,376,110, issued Mar. 8, 1983, to David et al., which is incorporated herein by reference. In the forward assay, each reagent is sequentially contacted with histone H1. If desired, separation of bound from unbound reagent can be performed before the addition of the next reagent. In a reverse assay, all reagents are pre-mixed prior to contacting histone H1. A modified reverse assay is described in U.S. Pat. No. 4,778, 751 issued Oct. 18, 1988, to El Shami et al., which is incorporated herein by reference. In a simultaneous assay, all reagents are separately but contemporaneously contacted with histone H1. As used herein, reagent means any component useful to perform the assays of the present invention, for example, the sample, histone H1, detectable secondary antibody, washing buffer or other solutions.

Separation steps for the various assay formats described herein, including the removal of unbound secondary antibody from the complex, can be performed by methods known in the art (Harlow and Lane, supra, 1988). For example, washing with a suitable buffer can be followed by filtration, aspiration or magnetic separation. If histone H1 or a pANCA-reactive fragment thereof is immobilized on a particulate support, such as on microparticles, the particulate material can be centrifuged, if desired, followed by removal of wash liquid. If histone H1 or a pANCA-reactive fragment thereof is immobilized on a membrane, filter or well, a vacuum or liquid absorbing apparatus can by applied to the opposite side of the membrane, filter or well to draw the wash liquid away from the complex.

The invention also provides methods of determining susceptibility to UC in an individual by obtaining a sample from the individual; contacting the sample with human histone H1, or pANCA-reactive fragment thereof, under conditions suitable to form a complex of human histone H1, or pANCA-reactive fragment thereof, and antibody to human histone H1; and detecting the presence or absence of the complex, where the presence of the complex indicates that the individual has increased susceptibility to UC. Susceptibility to UC in an individual also can be determined by obtaining a sample from the individual; contacting the sample with purified histone H1 isoform H1$^S$-2, or pANCA-reactive fragment thereof, under conditions suitable to form a complex of purified histone H1 isoform H1$^S$-2, or pANCA-reactive fragment thereof, and antibody to histone H1 isoform H1$^S$-2; and detecting the presence or absence of the complex, where the presence of the complex indicates that the individual has increased susceptibility to UC.

The term "individual," as used herein, means any animal capable of producing pANCA, including a human, non-human primate, rabbit, rat or mouse, provided that the animal does not have ulcerative colitis as defined by the clinical, endoscopic and histopathologic parameters disclosed herein. A sample to be assayed according to the methods of the invention can be obtained from any such individual.

As used herein, the term "susceptibility to UC," when used in reference to an individual, means an inability to resist ulcerative colitis disease-causing factors. As used herein, the term "increased susceptibility to UC," as indicated by the presence of a complex of histone H1 and antibody to histone H1, means an increased inability to resist ulcerative colitis disease-causing factors, as compared with an individual from whom a sample is obtained that does not form a complex when contacted with histone H1, or pANCA-reactive fragment thereof. Increased susceptibility to UC in an individual does not mean the individual will necessarily develop UC. However, increased susceptibility to UC in an individual is associated with an increased probability of having ulcerative colitis in the future.

The term "pANCA-reactive fragment of histone H1," as used herein, means a peptide or polypeptide that has an amino acid sequence having at least 80% identity to a portion of one of the amino acid sequences shown in FIG. 1 and pANCA-reactive activity as defined by the ability to form a complex with pANCA. A pANCA-reactive fragment of histone H1 can have from about three amino acids to about 200 amino acids. Preferably, a pANCA-reactive fragment of histone H1 has from about five to about fifty amino acids and most preferably from about eight to about twenty amino acids.

Several pANCA-reactive fragments of histone H1 are disclosed herein. As set forth in Examples II and III, peptides SEQ ID NO: 13, SEQ ID NO: 14 and SEQ ID NO: 20 are pANCA-reactive fragments of histone H1, identified by their reactivity with NANUC-1 and NANUC-2. Thus, pANCA-reactive fragments of histone H1 can include, for example, the amino acid sequence of SEQ ID NO: 7, SEQ ID NO: 13, SEQ ID NO: 14 or SEQ ID NO: 20. A pANCA-reactive fragment of histone H1 can have, for example, the amino acid sequence Pro-Lys-Lys-Ala-Lys-Lys-Pro-Ala-Ala-Ala-Thr-Val-Thr-Lys-Lys (SEQ ID NO: 20).

A pANCA-reactive fragment of histone H1 can be identified by the ability to form a complex with pANCA. For example, a pANCA-reactive fragment of histone H1 can be identified by its ability to form a complex with pANCA when contacted with pANCA-positive UC sera. Assays for the formation of an antigen-pANCA complex using pANCA-positive sera are well known in the art. For example, an enzyme-linked immunosorbent assay (ELISA) as described in Saxon et al., *J. Allergy Clin. Immunol.* 86:202–210 (1990), which is incorporated herein by reference, is particularly useful in identifying a pANCA-reactive fragment of histone H1 that forms a complex with pANCA.

A pANCA-reactive fragment of histone H1 further can be identified by its ability to form a complex with a representative UC pANCA monoclonal antibody, such as NANUC-2. The sequences of the NANUC-2 heavy and light chains are provided herein, and assays for determining binding to NANUC-2 are described in Examples IA and IB. An ELISA assay, for example, is particularly useful in identifying a pANCA-reactive fragment of histone H1. Example II describes identification of the pANCA-reactive fragments of histone H1 SEQ ID NO: 13 and SEQ ID NO: 14, and Example II describes identification of the pANCA-reactive fragment SEQ ID NO: 20 using ELISA analysis.

The present invention also provides methods of inducing tolerance in a pANCA-positive patient with UC by administering an effective dose of histone H1, or tolerogenic fragment thereof, to the pANCA-positive patient with UC. A tolerogenic fragment of histone H1 useful in the methods of the invention can include, for example, the amino acid sequence of SEQ ID NO: 7, SEQ ID NO: 13, SEQ ID NO: 14 or SEQ ID NO: 20. A particularly useful tolerogenic fragment of histone H1 includes the amino acid sequence of SEQ ID NO: 20. A tolerogenic fragment of histone H1 can be, for example, a 15-mer having amino acid sequence Pro-Lys-Lys-Ala-Lys-Lys-Pro-Ala-Ala-Ala-Thr-Val-Thr-Lys-Lys (SEQ ID NO: 20).

The term "tolerogenic fragment of histone H1," as used herein, means a peptide or polypeptide which has an amino acid sequence having at least 80% identity to a portion of one of the amino acid sequences shown in FIG. 1 and tolerogenic activity as defined by its ability either alone, or in combination with another molecule, to produce a decreased immunological response. A tolerogenic fragment of histone H1 has from about three amino acids to about 200 amino acids. Preferably, a tolerogenic fragment of histone H1 has from about five to about fifty amino acids and most preferably from about eight to about twenty amino acids.

A particularly useful tolerogenic fragment of histone H1 can be a cryptic T-cell determinant that normally is not the target of T-cell recognition due to inefficient processing and antigen presentation (see, for example, Sercarz et al., *Ann. Rev. Immunol.* 11:729 (1993), which is incorporated herein by reference). Without wishing to be bound by the following, ulcerative colitis can be associated with an immune response to histone H1 in disease tissue due to expression of a normally cryptic histone H1 T-cell determinant in an immunogenic form in disease target tissues but not in other tissues.

As disclosed herein, a variety of cell types have substantial amounts of NANUC-2 reactive histone H1, as assayed by Western analysis which involves denatured histone H1. In particular, all cell types assayed by Western analysis, including both hematopoietic and non-hematopoietic cells such as neutrophils, lymphocytes, Molt-4, HL60 promyelocytic leukemia and COS cells, have NANUC-2 reactive histone H1. However, as disclosed herein, only neutrophils and HL60 cells are reactive with NANUC-2 or UC sera when cells are methanol-fixed and assayed by an immunohistochemical analysis involving native protein. These results indicate that native, but not denatured, histone H1 can have different immunoaccessibility properties in neutrophilic and non-neutrophilic cell types.

The cell-type specific immunoaccessibility of histone H1 is supported by polyclonal rabbit anti-histone H1 antisera directed against an N-terminal 35 amino acid fragment of human histone H1 isoform $H1^{S}{}_{-2}$ (SEQ ID NO: 7). The antiserum against SEQ ID NO: 7 recognizes all histone H1 isoforms and has nearly identical reactivity profiles as NANUC-2 using Western analysis. Furthermore, the antisera against SEQ ID NO: 7, like pANCA-positive sera from UC patients, stains methanol-fixed neutrophils in a perinuclear distribution but not non-neutrophilic cells such as eosinophils or lymphocytes.

A tolerogenic fragment of histone H1 can be identified using a variety of assays, including in vitro assays such as T-cell proliferation or cytokine secretion assays and in vivo assays such as the induction of tolerance in murine models of ulcerative colitis. T-cell proliferation assays, for example, are well recognized in the art as predictive of tolerogenic activity (see, for example, Miyahara et al., *Immunol.* 86:110–115 (1995) or Lundin et al, *J. Exp. Med.* 178:187–196 (1993), each of which is incorporated herein by reference). A T-cell proliferation assay can be performed by culturing T-cells with irradiated antigen-presenting cells, such as normal spleen cells, in microtiter wells for 3 days with varying concentrations of a fragment of histone H1 to be assayed; adding $^3$H-thymidine; and measuring incorporation of $^3$H-thymidine into DNA. In such an assay, a fragment of histone H1 can be tested for activity, for example, at concentrations of 20 µg/ml and 40 µg/ml.

A tolerogenic fragment of histone H1 also can be identified using a T-cell cytokine secretion assay as is well known in the art. For example, T-cells can be cultured with irradiated antigen-presenting cells in microtiter wells with varying concentrations of a fragment of histone H1 and, after three days, the culture supernatants can be assayed for IL-2, IL-4 or IFN-γ as described in Czerinsky et al., *Immunol. Rev.* 119:5–22 (1991), which is incorporated herein by reference.

Primary T-cells for use in a T-cell proliferation assay or cytokine secretion assay, for example, can be isolated from lamina propria or peripheral blood. In addition, a convenient source of T-cells for use in an in vitro assay for tolerogenic activity can be a T-cell line established from an ulcerative colitis patient, murine model of ulcerative colitis or a healthy animal immunized with histone H1. A preferred source of T-cells for use in identifying a tolerogenic fragment of histone H1 is an ulcerative colitis patient.

A T-cell line can be established from a patient with UC, for example, by culturing T lymphocytes with about 1 µg/ml histone H1, which is prepared, for example, from human bone marrow as described in Example I, in the presence of low concentrations of growth-supporting IL-2 (about 10 µg/ml). A T-cell line can be established by culturing T lymphocytes with antigen-presenting cells and feeding the cells on an alternating four to five day cycle with either IL-2 and histone H1 or IL-2 alone as described in Nanda et al., *J. Exp. Med.* 176:297–302 (1992), which is incorporated herein by reference. A cell line that develops into a reliably proliferating cell line dependent on the presence of histone H1 is particularly useful in identifying tolerogenic fragments of histone H1. The establishment of T-cell lines from small intestinal mucosa is described, for example, in Lundin et al., supra, 1993.

A tolerogenic fragment of histone H1 can also be identified by its ability to induce tolerance in vivo, as indicated by a decreased immunological response, which can be a decreased T-cell response, such as a decreased proliferative response or cytokine secretion response as described above, or a decreased anti-histone H1 antibody titer. A neonatal or adult mouse can be tolerized with a fragment of histone H1, and a T-cell response or anti-histone H1 antibody titer can be assayed after challenging by immunization. For example, a neonatal mouse can be tolerized within 48 hours of birth by intraperitoneal administration of about 100 µg of a fragment of histone H1 emulsified with incomplete Freund's adjuvant and subsequently immunized with histone H1 at about 8 weeks of age (see, for example, Miyahara, supra, 1995). An adult mouse can be tolerized intravenously with about 0.33 mg of a fragment of histone H1, administered daily for three days (total dose 1 mg), and immunized one week later with histone H1. A decreased T-cell response, such as decreased proliferation or cytokine secretion, which indicates tolerogenic activity, can be measured using T-cells harvested 10 days after immunization. In addition, a decreased anti-histone H1 antibody titer, which also indicates tolerogenic activity, can be assayed using blood harvested 4–8 weeks after immunization. Methods for assaying a T-cell response or anti-histone H1 antibody titer are described above and are well known in the art.

A tolerogenic fragment of histone H1 also can be identified using a murine model of ulcerative colitis. Neonatal or adult mice having ulcerative colitis-like disease can be tolerized with a fragment of histone H1 as described above, and the T-cell response or anti-histone antibody titer assayed. A decreased T-cell response or decreased anti-histone H1 antibody titer indicates a decreased immunological response and, thus, serves to identify a tolerogenic fragment of histone H1. In addition, a tolerogenic fragment of histone H1 can be identified by the ability to reduce the frequency, time of onset or severity of colitis in a murine model of UC.

Several well-accepted murine models of ulcerative colitis are useful in identifying a tolerogenic fragment of histone H1. For example, mice deficient in IL-2 as described in Sadlack et al., *Cell* 75:253–261 (1993), which is incorporated herein by reference, and mice deficient in IL-10 as described in Kühn et al., *Cell* 75:263–274 (1993), which is incorporated herein by reference, have ulcerative-colitis like disease and are useful in identifying a tolerogenic fragment of histone H1. Furthermore, mice with mutations in T cell receptor (TCR) α, TCR β, TCR β×δ, or the class II major histocompatiblility complex (MHC) as described in Mombaerts et al., *Cell* 75:275–282 (1993), which is incorporated herein by reference, develop inflammatory bowel disease that resembles ulcerative colitis and, thus, are useful in identifying a tolerogenic fragment of histone H1. Similarly, a fragment of histone H1 can be assayed for tolerogenic activity in a SCID mouse reconstituted with CD45RB CD4+ T-cells, which is a well-accepted model of human ulcerative colitis, as described in Powrie et al., *Immunity* 1:553–562 (1994), which is incorporated herein by reference. Thus, a tolerogenic fragment of histone H1 readily can be identified by an in vitro or in vivo assay disclosed herein or by other assays well known in the art.

A pANCA-reactive or tolerogenic fragment of histone can be identified by screening, for example, fragments of histone H1 produced by chemical or proteolytic cleavage. A fragment prepared from histone H1 purified from a target tissue such as intestinal mucosa can be particularly useful since such a fragment can have a post-translational modification that contributes to pANCA-reactive activity or tolerogenic activity. Methods for chemical and proteolytic cleavage and for purification of the resultant protein fragments are well known in the art (see, for example, Deutscher, *Methods in Enzymology*, Vol. 182, "Guide to Protein Purification," San Diego: Academic Press, Inc. (1990), which is incorporated herein by reference). For example, a chemical such as cyanogen bromide or a protease such as trypsin, chymotrypsin, V8 protease, endoproteinase Lys-C, endoproteinase Arg-C or endoproteinase Asp-N can be used to produce convenient fragments of histone H1 that can be screened for pANCA-reactive activity or tolerogenic activity using one of the assays disclosed herein.

A pANCA-reactive or tolerogenic fragment of histone H1 also can be identified by screening a large collection, or library, of random peptides or peptides of interest for pANCA-reactive activity or tolerogenic activity. Peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid which encodes it. Methods for production of phage display libraries, including vectors and methods of diversifying the population of peptides which are expressed, are well known in the art (see, for example, Smith and Scott, *Methods Enzymol.* 217:228–257 (1993); Scott and Smith, *Science* 249:386–390 (1990); and Huse, WO 91/07141 and WO 91/07149, each of which is incorporated herein by reference). These or other well known methods can be used to produce a phage display library which can be screened, for example, with one of the disclosed assays for pANCA-reactive activity or tolerogenic activity. If desired, a population of peptides can be assayed for activity en masse. For example, to identify a pANCA-reactive fragment of histone H1, a population of peptides can be assayed for the ability to form a complex with NANUC-2; the active population can be subdivided and the assay repeated in order to isolate a pANCA-reactive fragment of histone H1 from the population.

In addition, a peptide library can be a panel of peptides spanning the entire sequence of a particular histone H1 isoform. For example, a panel of about 75 individual 15-mer peptides spanning the sequence of human histone H1 isoform $H1^S$-2 (SEQ ID NO: 2) can be synthesized, each overlapping by three residue shifts using the Mimotope cleavable pin technology (Cambridge Research Biochemicals, Wilmington, Del.), as described by Geysen et al., *Science* 235:1184 (1987), which is incorporated herein by reference. A panel of peptides spanning the sequence of any of the histone H1 isoforms such as those shown in FIG. 1 can be generated similarly, and the panel screened for pANCA-reactive activity or tolerogenic activity using one of the assays described above (see, for example, Miyahara et al., supra, 1995, which is incorporated herein by reference).

A library of peptides to be screened also can be made up of peptides of interest, such as a population of peptides related in amino acid sequence to SEQ ID NO: 7 or SEQ ID NO: 20 but having one or more amino acids that differ from SEQ ID NO: 7 or SEQ ID NO: 20. For identifying a tolerogenic fragment of histone H1, peptides of interest also can be peptides derived from a histone H1 sequence that have appropriate HLA-DR binding motifs as described, for example, in Sette et al., *J. Immunol.* 151:3163–3170 (1993), which is incorporated herein by reference. A particularly useful population of peptides is a population having a HLA-DR2 binding motif (Yang et al., supra, 1993). If desired, peptides of interest can be selected for HLA-DR binding activity as described in Sette et al., supra, 1993, prior to screening for tolerogenic activity.

As used herein, the term "fragment" means a peptide, polypeptide or compound containing naturally occurring amino acids, non-naturally occurring amino acids or chemically modified amino acids. A pANCA-reactive or tolerogenic fragment of histone H1 also can be a peptide mimetic, which is a non-amino acid chemical structure that mimics the structure of a peptide having an amino acid sequence derived from histone H1, provided that the peptidomimetic retains pANCA-reactive activity or tolerogenic activity, as defined herein. Such a mimetic generally is characterized as exhibiting similar physical characteristics such as size, charge or hydrophobicity in the same spatial arrangement found in its peptide counterpart. A specific example of a peptide mimetic is a compound in which the amide bond between one or more of the amino acids is replaced, for example, by a carbon-carbon bond or other bond well known in the art (see, for example, Sawyer, *Peptide Based Drug Design*, ACS, Washington (1995), which is incorporated herein by reference).

As used herein, the term "amino acid" refers to one of the twenty naturally occurring amino acids, including, unless stated otherwise, L-amino acids and D-amino acids. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains pANCA-reactive activity or tolerogenic activity. Examples of amino acids and amino acids analogs are listed in Gross and Meienhofer, *The Peptides: Analysis, Synthesis, Biology*, Academic Press, Inc., New York (1983), which is incorporated herein by reference. An amino acid also can be an amino acid mimetic, which is a structure that exhibits substantially the same spatial arrangement of functional groups as an amino acid but does not necessarily have both the α-amino and α-carboxyl groups characteristic of an amino acid.

A pANCA-reactive or tolerogenic fragment of histone H1 useful in the invention can be produced or synthesized using methods well known in the art. Such methods include recombinant DNA methods and chemical synthesis methods for production of a peptide. Recombinant methods of producing a peptide through expression of a nucleic acid sequence encoding the peptide in a suitable host cell are well known in the art and are described, for example, in Sambrook et al., *Molecular Cloning: A Laboratory Manual,* 2nd Ed, Vols 1 to 3, Cold Spring Harbor Laboratory Press, New York (1989), which is incorporated herein by reference. Nucleic acids encoding histone H1 are available to one skilled in the art as described in Eick et al., *Eur. J. Cell. Biol.* 49:110–115 (1989); Albig et al., *Genomics* 10:940–948 (1991); Carozzi et al., *Science* 224:1115–1117 (1984); La Bella et al., *J. Biol. Chem.* 263:2115–2118 (1988); Cole et al., *Gene* 89:265–269 (1990); Cheng et al., *Proc. Natl. Acad. Sci. USA* 86:7002–7006 (1989); Yan et al., *J. Biol. Chem.* 262:17118–17125 (1987); and Brown and Sitman, *J. Biol. Chem.* 268:713–718 (1993), each of which is incorporated herein by reference.

A pANCA-reactive or tolerogenic fragment of histone H1 useful in the invention also can be produced by chemical synthesis, for example, by the solid phase peptide synthesis method of Merrifield et al., *J. Am. Chem. Soc.* 85:2149 (1964), which is incorporated herein by reference. Standard solution methods well known in the art also can be used to synthesize a pANCA-reactive or tolerogenic fragment of histone H1 useful in the invention (see, for example, Bodanszky, *Principles of Peptide Synthesis*, Springer-Verlag, Berlin (1984) and Bodanszky, *Peptide Chemistry*, Springer-Verlag, Berlin (1993), each of which is incorporated herein by reference). A newly synthesized peptide can be purified, for example, by high performance liquid chromatography (HPLC), and can be characterized using, for example, mass spectrometry or amino acid sequence analysis.

It is understood that limited modifications can be made to histone H1 without destroying its biological function. Similarly, limited modifications can be made to a pANCA-reactive fragment of histone H1 or a tolerogenic fragment of histone H1 without destroying its pANCA-reactive activity or tolerogenic activity. A modification of histone H1 that does not destroy pANCA-reactive activity or a modification of histone H1 that does not destroy tolerogenic activity is within the definition of histone H1. Similarly, a modification of a pANCA-reactive fragment of histone H1 that does not destroy its ability to form a complex with pANCA is within the definition of a pANCA-reactive fragment of histone H1. Furthermore, a modification of a tolerogenic fragment of histone H1 that does not destroy its ability to produce a decreased immunological response is within the definition of a tolerogenic fragment of histone H1. A modification can be, for example, an addition, deletion, or substitution of amino acid residues; substitution of a compound that mimics amino acid structure or function; or addition of chemical moieties such as amino or acetyl groups. The activity of a modified histone H1 or a modified fragment of histone H1 can be assayed, for example, using one of the assays for pANCA-reactive or tolerogenic activity disclosed herein.

A particularly useful modification of histone H1 or a pANCA-reactive or tolerogenic fragment of histone H1 is a modification that confers, for example, increased stability. Incorporation of one or more D-amino acids is a modification useful in increasing stability of a protein or protein fragment. Similarly, deletion or substitution of lysine can increase stability by protecting against degradation. For example, such a substitution can increase stability and, thus, bioavailability of histone H1 or a tolerogenic fragment of histone H1, provided that the substitution does not affect tolerogenic activity.

As used herein, the term "effective dose" means the amount of histone H1 or tolerogenic fragment thereof useful for inducing tolerance in a pANCA-positive patient with UC. For induction of oral tolerance, for example, multiple smaller oral doses can be administered or a large dose can be administered. Such doses can be extrapolated, for example, from the induction of tolerance in animal models (see, for example, Trentham et al., *Science* 261:1727–1730 (1993), which is incorporated herein by reference).

The present invention also provides a method of inducing tolerance in a pANCA-positive patient with UC by removing sera from the patient; contacting the sera with histone H1, or a pANCA-reactive fragment thereof, under conditions suitable to form a complex of human histone H1, or pANCA-reactive fragment thereof, and pANCA; separating the complex from sera lacking the complex; and returning the sera lacking the complex to the patient.

In addition, the invention provides a composition of histone H1, or fragment thereof, and a tolerogizing molecule. A composition of the invention can contain a fragment of histone H1 including the amino acid sequence of SEQ ID NO: 7, SEQ ID NO: 13, SEQ ID NO: 14 or SEQ ID NO: 20 combined with a tolerogizing molecule. A composition of the invention also can contain a fragment of histone H1 having the amino acid sequence of SEQ ID NO: 20 combined with a tolerogizing molecule.

Various molecules are known in the art to cause, promote or enhance tolerance. See, for example, U.S. Pat. No. 5,268,454, and citations therein, which are incorporated herein by reference. As used herein, the term "tolerogizing molecule" means a molecule, compound or polymer that causes, promotes or enhances tolerogenic activity when combined with histone H1, or fragment thereof. A tolerogizing molecule can be, for example, conjugated to histone H1, or fragment thereof. Such tolerogizing molecules include, for example, polyethylene glycol and are well known in the art (see, for example, U.S. Pat. No. 5,268,454, supra).

An effective dose of histone H1 or tolerogenic fragment thereof for inducing tolerance can be administered by methods well known in the art. Oral tolerance is well-recognized in the art as a method of treating autoimmune disease (see, for example, Weiner, *Hospital Practice*, pp. 53–58 (Sep. 15, 1995), which is incorporated herein by reference). For example, orally administered autoantigens suppress several experimental autoimmune models in a disease- and antigen-specific fashion; the diseases include experimental autoimmune encephalomyelitis, uveitis, and myasthenia, collagen- and adjuvant-induced arthritis, and diabetes in the NOD mouse (see, for example, Weiner et al., *Ann. Rev. Immunol.* 12:809–837 (1994), which is incorporated herein by reference). Furthermore, clinical trials of oral tolerance have produced positive results in treating multiple sclerosis, rheumatoid arthritis and uveitis. In addition, parenteral administration of histone H1, or tolerogenic fragment thereof, can be used to induce tolerance. Subcutaneous injection, for example, can be used to deliver histone H1, or tolerogenic fragment thereof, to a pANCA-positive patient with UC (Johnson, *Ann. Neurology* 36(suppl.):S115–S117 (1994), which is incorporated herein by reference).

The invention also provides methods of preventing UC in an individual by administering an effective dose of histone H1, or tolerogenic fragment thereof, to the individual. The methods of the invention are particularly useful for preventing UC in an individual having increased susceptibility to UC. Such methods can be particularly useful for preventing UC when an effective dose of histone H1 or tolerogenic fragment thereof is administered to a newborn individual.

The following examples are intended to illustrate but not limit the present invention.

EXAMPLE I

Identification of the Ulcerative Colitis pANCA Target Antigen

This example demonstrates that representative UC pANCA monoclonal antibodies bind histone H1 specifically.

A. Histone H1 is an ulcerative colitis pANCA target antigen

Representative UC pANCA monoclonal antibodies, designated NANUC-1 and NANUC-2, were isolated from a UC lamina propria lymphocyte phage display IgG library and use to screen human neutrophil. Western analysis demonstrated specific binding of NANUC-2 to a nuclear protein doublet of 32–33 kDa. Purification by subcellular fractionation and preparative gel electrophoresis followed by protein microsequencing identified the NANUC-2 reactive antigen as histone H1.

Western analysis showed reactivity with lysine-rich calf thymus histone. In addition, histones purified from human neutrophil were fractionated into a perchloric acid insoluble fraction (containing core histones) and a perchloric acid soluble fraction (containing histone H1). As shown in FIG. 2, NANUC-2 reacted with the perchloric acid soluble histone fraction, indicating that histone H1 is an ulcerative colitis pANCA target antigen. Purified core histones (H2A, H2B, H3 and H4) were minimally reactive with NANUC-2. In addition, purified human histone H1 isoforms $H1^S$-1, $H1^S$-2, $H1^S$-3, $H1^S$-4 and $H1^o$ were analyzed by immunoblot analysis, and NANUC-2 was reactive with each of the isoforms including $H1^o$.

Histone H1 was purified according to the methods described in Prescott, *Methods in Cell Biology*, Vol XVI, "Chromatin and Chromosomal Protein Research" (New York, N.Y.: Academic Press (1977)), which is incorporated herein by reference, as follows. Purified bone marrow was obtained and red blood cell lysed prior to freezing. The bone marrow, which contained lymphocytes and granulocytes, was thawed rapidly and washed with phosphate-buffered saline (PBS). The cells were extracted with four cell volumes of 200 mM $H_2SO_4$/40 mM $NaHSO_3$ in the presence of protease inhibitors, sonicated for 60 seconds on ice, and incubated on ice for one hour with occasional vortexing. Nuclei and cell debris were pelleted at 2500 rpm (Beckman JA-6) at 4° C. for 20 minutes, the supernatant transferred to a new tube, and core histones (H2A, H2A, H3 and H4) precipitated at –20° C. overnight by the addition of three to four volumes of 95% ethanol. The histone pellet was washed with 70% ethanol, dried and resuspended in 3 ml 40 mM $NaHSO_3$ with protease inhibitors.

Histone H1 was selectively extracted from core histones by addition of 70% perchloric acid (to a final concentration of 5%) followed by incubation on a rotating wheel at 4° C. for 1 hour. Core histones were pelleted at 2500 rpm at 4° C. for 20 minutes. Histone H1 was precipitated from the supernatant for 2 hours at –20° C. with 10 ml of acidified acetone (10 ml acetone +77 µl concentrated hydrochloric acid). Histone H1 was centrifuged as above, and the pellet washed with a solution of 3.5 ml acetone/1 ml 1M HCl to remove high-mobility group (HMG) proteins. The core histones and histone H1 pellets each were washed separately three times with 5 ml 95% ethanol and dried. Protein purity was established by polyacrylamide gel electrophoresis and Coomassie blue staining.

Western analysis was performed as follows. Cells were lysed in 10 mM HEPES/1.5 mM $MgCl_2$/10 mM KCl pH7.9 in the presence of protease inhibitors and sheared with a 20 G needle. Lysis was monitored by trypan blue exclusion. Nuclei were pelleted and resuspended in extraction buffer, and the cell fractions electrophoresed on a 12% polyacrylamide gel under non-reducing conditions. Proteins were transferred to nitrocellulose membranes, and the transfer verified by Ponceau S red staining (SIGMA, St. Louis, Mo.). Membranes were blocked with 5% milk in 0.1% Tween-20/PBS for 1 hour. Primary and secondary antibody incubations were for 1 hour in 1% milk in 0.1% Tween-20/PBS. The primary antibodies, NANUC-1, NANUC-2, and anti-tetanus toxoid Fabs were used at a concentration of 0.1 to 1.0 µg/ml. The secondary antibody was goat anti-human Fab-alkaline phosphatase or goat anti-human kappa-biotin used at a dilution of 1 to 1000 or 1 to 2000, respectively. Alkaline phosphatase labeled antibodies were detected with BCIP-NBT (SIGMA). Biotinylated antibodies were detected with SA-HRP (Amersham Lifesciences, Inc., Arlington Heights, Ill.) and enhanced chemiluminescence.

B. Reactivity of NANUC-2 with histone H1 using ELISA analysis

Microtiter plates coated with neutrophil, total histone or purified calf thymus histone H1 were used for ELISA analysis as described below. The reactivity of NANUC-1, NANUC-2 and negative control anti-tetanus toxoid antibody was tested against human PMN (neutrophil), total histone, calf thymus histone H1, or tetanus toxoid antigen. As shown in FIG. 3, the ELISA assays demonstrated that NANUC-1 and NANUC-2 react with human neutrophil. However, NANUC-2, but not NANUC-1 or anti-tetanus toxoid antibody, was reactive with total calf thymus histone (histone H1 and core histones) and calf thymus histone H1 (SIGMA).

ELISA assays were performed as follows. For detection of total Fab immunoglobulin, microtiter plates (Costar 3069, Cambridge, Mass.) were coated overnight at 4° C. with 500 ng/well antigen in bicarbonate pH 9.6 coating buffer. Wells were blocked with 0.25% BSA/PBS for 1 hour, incubated with rFabs diluted in 0.25% BSA/PBS for 1 hour, and washed five times with 0.5% Tween-20/PBS at room temperature. Plates were subsequently incubated with a 1 to 1000 dilution of alkaline phosphatase-labeled goat anti-human Fab (Pierce, Rockford, Ill.) for 1 hour; washed five times in 0.5% Tween-20/PBS; washed three times with Tris-NaCl (50 mM Tris 150 mM NaCl pH 7.5); and developed with 5 mg/ml p-nitrophenyl phosphate (SIGMA) in 10% diethanolamine/1 mM $MgCl_2$ pH 9.8. The absorbance of each sample was measured at 405 nm using a Biorad ELISA reader (Richmond, Calif.). Neutrophil samples were prepared as described in Saxon et al., supra, 1990; total calf thymus histone and calf thymus histone H1were obtained from SIGMA.

C. Reactivity of NANUC-2 with subcellular fractions

Figure 4A:
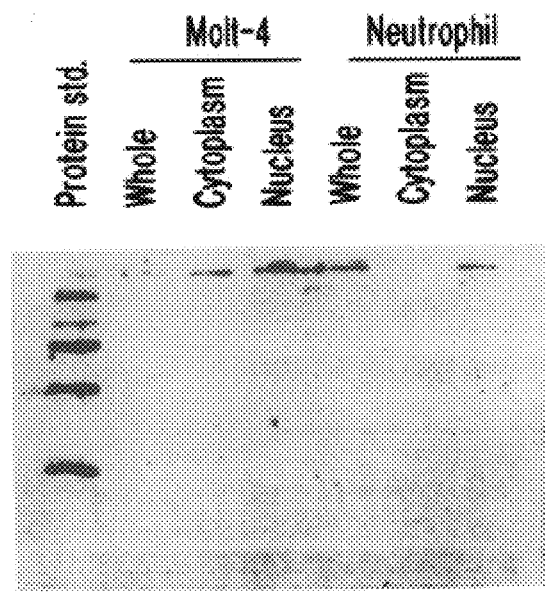
FIG. 4A shows Western analysis of blots of whole cell, nuclear and cytoplasmic fractions of Molt-4 cells and human neutrophils each reacting with NANUC-1.
Figure 4B:
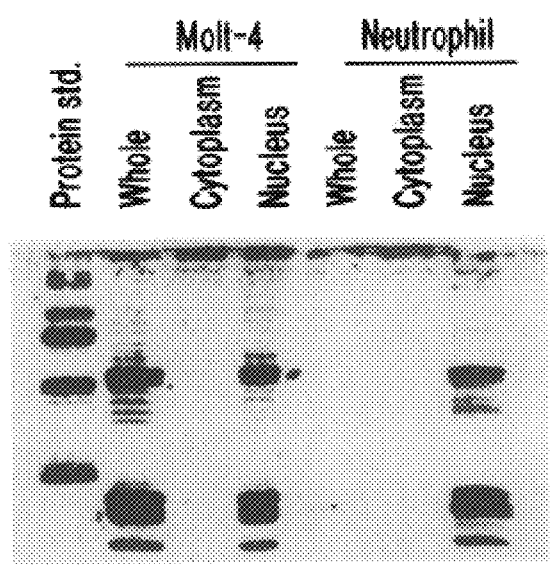
FIG. 4B shows Western analysis of blots of whole cell, nuclear and cytoplasmic fractions of Molt-4 cells and human neutrophils (identical to the blots shown in FIG. 4A) each reacting with NANUC-2.
Figure 4C:
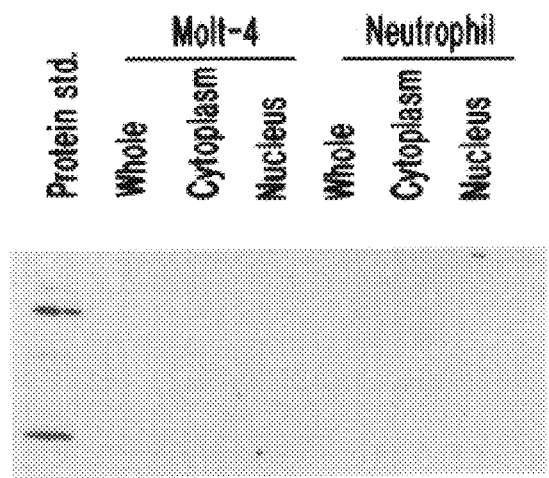
FIG. 4C shows Western analysis of blots of whole cell, nuclear and cytoplasmic fractions of Molt-4 cells and human neutrophils (identical to the blots shown in FIGS. 4A and 4B) each reacting with negative control anti-tetanus toxoid antibody (TT).
Figure 5A:
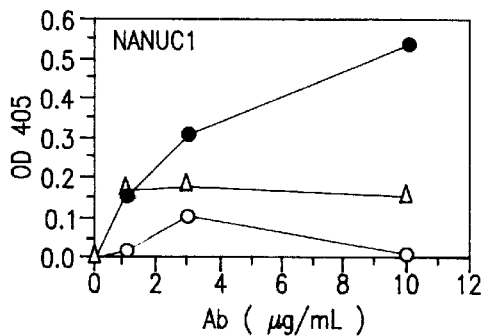
FIG. 5A shows the reactivity of histone derived peptides (SEQ ID NOS: 19 to 21) with the NANUC-1 antibody.
Figure 5D:
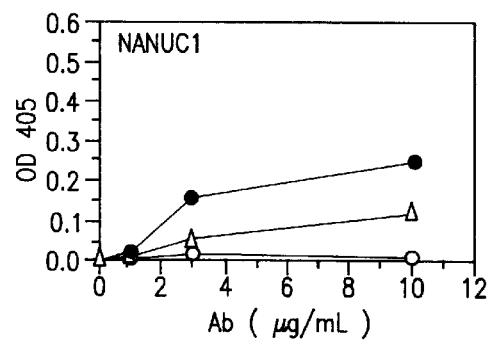
FIG. 5D shows the reactivity of histone derived peptides (SEQ ID NOS: 16 to 18) with the NANUC-1 antibody.
Figure 5B:
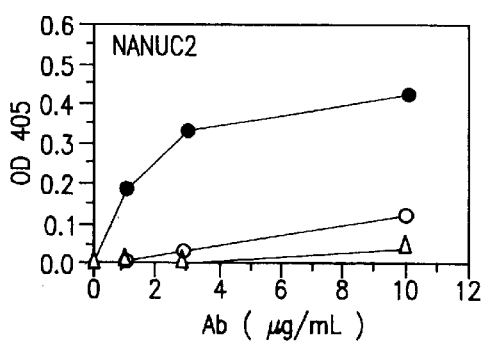
FIG. 5B shows the reactivity of histone derived peptides (SEQ ID NOS: 19 to 21) with the NANUC-2 antibody.
Figure 5E:
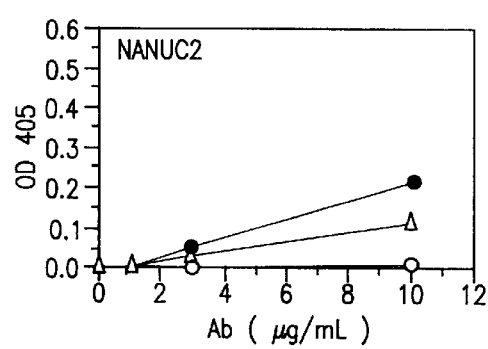
FIG. 5E shows the reactivity of histone derived peptides (SEQ ID NOS: 16 to 18) with the NANUC-2 antibody.
Figure 5C:
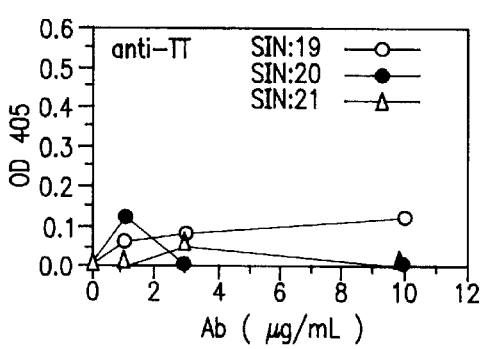
FIG. 5C shows the reactivity of histone derived peptides (SEQ ID NOS: 19 to 21) with anti-tetanus toxoid antibody (anti-TT).
Figure 5F:
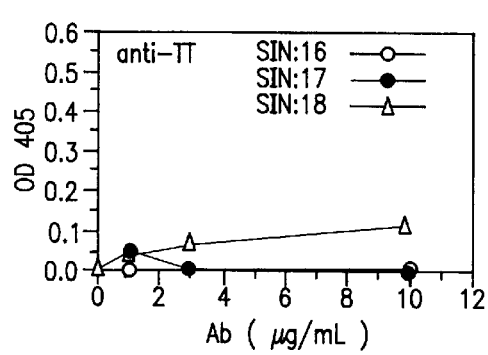
FIG. 5F shows the reactivity of histone derived peptides (SEQ ID NOS: 16 to 18) with anti-tetanus toxoid antibody (anti-TT).

Subcellular fractionation of human neutrophils demonstrated that NANUC-2 is almost exclusively reactive with a nuclear protein doublet of 32–33 kDa apparent molecular weight (see FIG. 4). The NANUC-2 reactive doublet was present in the nuclear fraction of neutrophils and represents histone H1 subtypes $H1^S$-1, $H1^S$-2, $H1^S$-3, $H1^S$-4 and $H1^o$ as determined by apparent size on SDS-PAGE following Western blot detection. Additional lower molecular weight proteins, which have slight reactivity with NANUC-2, may represent the core histones or histone H1 degradation products. NANUC-1 and the negative control anti-tetanus toxoid antibody were not reactive with any protein species on Western blots.

In cell types other than neutrophils, histone H1 reactivity was detected in both whole cell lysate and nuclear fraction but not in the cytoplasmic fraction. In contrast, neutrophil nuclear fraction revealed a large amount of NANUC-2 reactive histone H1, but no reactivity was seen in whole cell lysate prepared from the same cells. The lack of reactivity in neutrophil whole cell lysate can be a result of very rapid degradation of histone H1 by proteases found in neutrophilic granules but not in other cells such as Molt-4 cells (see FIG. 4).

EXAMPLE II

Identification of pANCA-Reactive H1 Fragments

This example demonstrates that particular fragments of histone H1 are reactive with the NANUC-2 antibody.

To further characterize the pANCA-reactive histone H1 epitope, purified protein was subjected to chemical cleavage with N-N bromosuccinamide (NBS) and proteolysis with chymotryspin, and reactivity of the resulting fragments was analyzed by silver staining and immunoblotting. NBS cleavage of H1 resulted in two fragments: an N-terminal 73 amino acid fragment (SEQ ID NO: 12) and a C-terminal 147 amino acid fragment (SEQ ID NO: 13). Because of the extremely charged nature of these fragments, the apparent mobilities of the 73 and 147 amino acid fragments are 23 and 11 kD, respectively. Immunoblot analysis revealed that only the larger 147 amino acid fragment (SEQ ID NO: 13) was reactive with NANUC-2, indicating that a pANCA-reactive epitope lies within the carboxy-terminal 147 amino acids. Chymotrypsin digests the N-terminal portion of the 147 amino carboxy-terminal fragment, producing a fragment with an apparent molecular weight of 17 kD. Immunoblots of chymotrypsin-digested H1 revealed NANUC-2 reactivity only with the carboxy-terminal fragment, thereby narrowing the pANCA-reactive epitope to the carboxy-terminal 113 amino acids (SEQ ID NO: 14). As a control to show that the nonreactive N-terminal fragments were properly transferred, the same blots showed reactivity with a rabbit anti-H1-3 polyclonal specific for the N-terminal fragment (see Parseghian et al., *Chromosoma* 103:198 (1994) and Parseghian et al., *Chrom. Res.* 1:127 (1993), each of which is incorporated herein by reference).

H1 epitopes were mapped using N-N bromosuccinamide and chymotrypsin proteolysis with a procedure modified from Parseghian et al., supra, 1993; Sherod et al., *J. Biol Chem.* 12:3923 (1974) and Costa et al., *Clin. Exp. Immunol.* 63: 608 (1986), each of which is incorporated herein by reference. Briefly, in a 10 μl reaction, 12 μg of bone marrow histone H1 was cleaved with 0.85 μg N-N bromosuccinamide (Sigma) in 0.9 N acetic acid. The reaction was terminated at varying time points by transferring 2.5 μL aliquots into 7.5 μl stop buffer (0.125 M Tris Cl pH 7.6 with 10.7 μg tyrosine (Sigma)). Chymotrypsin cleavage was performed in a 10 μl reaction volume by incubating 6 μg bone marrow histone H1 with 0.01 μg chymotrypsin (Boehringer Mannheim, Indianapolis, Ind.) in 0.1 M Tris-Cl pH 8.0, 10 mM CaCl. Reactions were stopped at various time points by addition of 1 μl 20 mM phenyl methyl sulfonyl fluoride (PMSF; Boehringer Mannheim), and 1.5 μg of NBS and chymotryptic H1 fragments diluted in Laemli buffer were run on 13% acrylamide gels using a Biorad mini gel apparatus, transferred to nitrocellulose, and immunoblotted as described above. Gels were silver stained using a Biorad silver stain kit (Biorad, Richmond, Calif.).

EXAMPLE III

Identification of pANCA-Reactive Peptides Derived From Histone H1

This example demonstrates that synthetic peptides spanning histone H1 can be assayed for NANUC-1 and NANUC-2 binding to identify pANCA-reactive peptides.

Overlapping 15-mer peptides that spanned the C-terminal 109 amino acids of the human H1$^S$-3 gene product with an N-terminal biotin were synthesized (P. Allen, Washington University, St. Louis). Each of the peptides overlapped adjacent peptide sequences by five amino acids except for peptide SEQ ID NO: 25. The eleven peptide sequences are shown in Table 2.

Peptides were tested for binding to 1.0, 3.0 and 10.0 μg/ml NANUC-1, NANUC-2 and negative control anti-tetanus toxoid antibody P313 (anti-TT). As shown in FIG. 5, peptide SEQ ID NO: 20 was distinguished among the 11 peptides assayed by significant binding to NANUC-1 and NANUC-2 ($OD_{405}$ of approximately 0.5; significant at 1.0 μg/ml) compared to background levels observed with the rFab negative control anti-TT antibody, yielding an $OD_{405}$ of less than 0.1. Neither of the two adjacent, overlapping peptides SEQ ID NO: 19 or SEQ ID NO: 21 showed significant binding to both

TABLE 2

| Histone H1 peptide sequences | |
|---|---|
| SEQ ID NO: | Amino acid sequence |
| SEQ ID NO: 15 | FKLNKKAASGEAKPK |
| SEQ ID NO: 16 | EAKPKVKKAGGTKPK |
| SEQ ID NO: 17 | GTKPKKPVGAAKKPK |
| SEQ ID NO: 18 | AKKPKKAAGGATPKK |
| SEQ ID NO: 19 | ATPKKSAKKTPKKAK |
| SEQ ID NO: 20 | PKKAKKPAAATVTKK |
| SEQ ID NO: 21 | TVTKKVAKSPKKAKV |
| SEQ ID NO: 22 | KKAKVAKPKKAAKSA |
| SEQ ID NO: 23 | AAKSAAKAVKPKAAK |
| SEQ ID NO: 24 | PKAAKPKVVKPKKAA |
| SEQ ID NO: 25 | KPKVVKPKKAAPKKK |

NANUC antibodies. Peptide SEQ ID NO: 17 also reacted with NANUC-1 and NANUC-1; however, this binding was weaker ($OD_{405}$ of approximately 0.25 for both NANUC antibodies) than the reactivity seen with peptide SEQ ID NO: 20.

These data indicate that histone H1 peptide PKKAKKPAAATVTKK (SEQ ID NO: 20) is specifically reactive with two distinct UCpANCA monoclonal antibodies. Because adjacent peptides lack activity, the pANCA reactivity of peptide SEQ ID NO: 20 may depend on its unique internal linear amino acid sequence KPAAA (SEQ ID NO: 26) or may depend on the unique conformation of the peptide sequence SEQ ID NO: 20 in its entirety.

The eleven H1 peptides SEQ ID NOS: 15 to 25 were assayed for reactivity with UCpANCA monoclonal antibodies NANUC-1 and NANUC-2 as follows. ELISA wells were coated with 50 μl solution of the H1 peptide of interest (at a concentration of 250 μg/ml) in carbonate buffer, pH 9.6, overnight at 4° C. Wells were blocked with phosphate buffered saline/0.5% Tween-20/500 μg/ml bovine serum albumin (BSA; SIGMA) for 1 hour at room temperature. Wells were washed five times with 0.05% Tween-20 in PBS (wash buffer), then reacted with rFab antibody diluted in wash buffer at indicated concentrations for 2 hours at room temperature. Plates were washed five times, and immunocomplexes detected subsequently with 0.05% alkaline phosphatase-conjugated goat anti-human Fab (Pierce) in wash buffer for 1 hour at room temperature. After washing, the samples were reacted with BCIP-NBT substrate (SIGMA). FIG. 5 shows the absorbance at 405 nm ($OD_{405}$) after normalization for background binding due to reactivity with secondary antibody alone.

All journal article, reference and patent citations provided above, in parentheses or otherwise, whether previously stated or not, are incorporated herein by reference in their entirety.

Although the invention has been described with reference to the examples above, it should be understood that various modifications can be made without departing from the spirit of the invention. Accordingly, the invention is limited only by the following claims.

We claim:

1. A method of diagnosing ulcerative colitis (UC) in a subject suspected of having inflammatory bowel disease, comprising:

(a) obtaining a sample from said subject;

(b) contacting said sample with a substantially purified histone H1 polypeptide having an amino acid sequence selected from the group consisting of SEQ ID NOS: 1 to 6, or a modification or fragment thereof having immunological reactivity with pANCA, under conditions suitable to form a complex of said histone H1, or modification or fragment thereof, with antibody to histone H1; and (c) detecting the presence or absence of said complex, wherein the presence of said complex indicates that said subject has UC.

2. The method of claim 1, wherein the presence or absence of said complex is detected with a detectable secondary antibody, wherein said detectable secondary antibody has specificity for a class determining portion of said antibody to histone H1.

3. The method of claim 1, wherein said histone H1 is human histone H1 having an amino acid sequence selected from the group consisting of SEQ ID NOS: 1 to 6.

4. A method of diagnosing UC in a subject suspected of having inflammatory bowel disease, comprising:

(a) obtaining a sample from said subject;

(b) contacting said sample with purified histone H1 isoform $H1^S$-2 having the amino acid sequence of SEQ ID NO: 2, or a modification or fragment thereof having immunological reactivity with pANCA, under conditions suitable to form a complex of said histone H1 isoform $H1^S$-2, or modification or fragment thereof, with antibody to histone H1 isoform $H1^S$-2; and (c) detecting the presence or absence of said complex, wherein the presence of said complex indicates that said subject has UC.

5. The method of claim 4, wherein the presence or absence of said complex is detected with a detectable secondary antibody, wherein said detectable secondary antibody has specificity for a class determining portion of said antibody to histone H1 isoform $H1^S$-2.

6. The method of claim 5, wherein said fragment comprises an amino acid sequence selected from the group consisting of SEQ ID NO: 7, SEQ ID NO: 13, SEQ ID NO: 14 and SEQ ID NO: 20.

7. The method of claim 6, wherein said fragment has the amino acid sequence of SEQ ID NO: 20.

8. A method of diagnosing a perinuclear anti-neutrophil cytoplasmic antibody-positive (pANCA-positive) clinical subtype of UC in a patient with UC, comprising:

(a) obtaining a sample from said patient with UC;

(b) contacting said sample with a substantially purified histone H1 polypeptide having an amino acid sequence selected from the group consisting of SEQ ID NOS: 1 to 6, or a modification or fragment thereof having immunological reactivity with pANCA, under conditions suitable to form a complex of said histone H1, or modification or fragment thereof, with antibody to histone H1; and (c) detecting the presence or absence of said complex, wherein the presence of said complex indicates that said patient has said pANCA-positive clinical subtype of UC.

9. The method of claim 8, wherein the presence or absence of said complex is detected with a detectable secondary antibody, wherein said detectable secondary antibody has specificity for a class determining portion of said antibody to histone H1.

10. The method of claim 8, wherein said histone H1 is human histone H1 having an amino acid sequence selected from the group consisting of SEQ ID NOS: 1 to 6.

11. A method of diagnosing a pANCA-positive clinical subtype of UC in a patient with UC, comprising:

(a) obtaining a sample from said patient with UC;

(b) contacting said sample with purified histone H1 isoform $H1^S$-2 having the amino acid sequence of SEQ ID NO: 2, or a modification or fragment thereof having immunological reactivity with pANCA, under conditions suitable to form a complex of said histone H1 isoform $H1^S$-2, or modification or fragment thereof, with antibody to histone H1 isoform $H1^S$-2; and (c) detecting the presence or absence of said complex, wherein the presence of said complex indicates that said patient has said pANCA-positive clinical subtype of UC.

12. The method of claim 11, wherein the presence or absence of said complex is detected with a detectable secondary antibody, wherein said detectable secondary antibody has specificity for a class determining portion of said antibody to histone H1 isoform $H1^S$-2.

13. The method of claim 12, wherein said fragment comprises an amino acid sequence selected from the group consisting of SEQ ID NO: 7, SEQ ID NO: 13, SEQ ID NO: 14 and SEQ ID NO: 20.

14. The method of claim 13, wherein said fragment has the amino acid sequence of SEQ ID NO: 20.

15. A method of determining susceptibility to UC in an individual, comprising:

(a) obtaining a sample from said individual;

(b) contacting said sample with a substantially purified histone H1 polypeptide having an amino acid sequence selected from the group consisting of SEQ ID NOS: 1 to 6, or a modification or fragment thereof having immunological reactivity with pANCA, under conditions suitable to form a complex of said histone H1, or modification or fragment thereof, with antibody to histone H1; and (c) detecting the presence or absence of said complex, wherein the presence of said complex indicates that said individual has increased susceptibility to UC.

16. The method of claim 15, wherein the presence or absence of said complex is detected with a detectable secondary antibody, wherein said detectable secondary antibody has specificity for a class determining portion of said antibody to histone H1.

17. The method of claim 15, wherein said histone H1 is human histone H1 having amino acid sequence selected from the group consisting of SEQ ID NOS: 1 to 6.

18. A method of determining susceptibility to UC in an individual, comprising:

(a) obtaining a sample from said individual;

(b) contacting said sample with purified histone H1 isoform $H1^S$-2 having the amino acid sequence of SEQ ID NO: 2, or a modification or fragment thereof having immunological reactivity with pANCA, under conditions suitable to form a complex of said histone H1 isoform $H1^S$-2, or modification or fragment thereof, with antibody to histone H1 isoform $H1^S$-2; and (c) detecting the presence or absence of said complex, wherein the presence of said complex indicates that said individual has increased susceptibility to UC.

19. The method of claim 18, wherein the presence or absence of said complex is detected with a detectable secondary antibody, wherein said detectable secondary antibody has specificity for a class determining portion of said antibody to histone H1 isoform $H1^S$-2.

20. The method of claim 19, wherein said fragment comprises an amino acid sequence selected from the group consisting of SEQ ID NO: 7, SEQ ID NO: 13, SEQ ID NO: 14 and SEQ ID NO: 20.

21. The method of claim 20, wherein said fragment has the amino acid sequence of SEQ ID NO: 20.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 212 amino acids
      (B) TYPE: amino acid
      (D) TOPOLOGY: linear (ix) FEATURE:
      (A) NAME/KEY: Peptide
      (B) LOCATION: 1..212
      (D) OTHER INFORMATION: /note= "product = Human Histone H1-S-1"

(xi) SEQUENCE DESCRIPTION: SEQ ID NO:1:

```
Ser Glu Thr Ala Pro Ala Ala Pro Ala Ala Ala Pro Pro Ala Glu Lys
1               5                   10                  15

Ala Pro Val Lys Lys Lys Ala Ala Lys Lys Ala Gly Gly Thr Pro Arg
            20                  25                  30

Lys Ala Ser Gly Pro Pro Val Ser Glu Leu Ile Thr Lys Ala Val Ala
        35                  40                  45

Ala Ser Lys Glu Arg Ser Gly Val Ser Leu Ala Ala Leu Lys Lys Ala
    50                  55                  60

Leu Ala Ala Ala Gly Tyr Asp Val Glu Lys Asn Asn Ser Arg Ile Lys
65                  70                  75                  80

Leu Gly Leu Lys Ser Leu Val Ser Lys Gly Thr Leu Val Gln Thr Lys
                85                  90                  95

Gly Thr Gly Ala Ser Gly Ser Phe Lys Leu Asn Lys Lys Ala Ala Ser
            100                 105                 110

Gly Glu Ala Lys Pro Lys Val Lys Lys Ala Gly Gly Thr Lys Pro Lys
        115                 120                 125

Lys Pro Val Gly Ala Ala Lys Lys Pro Lys Lys Ala Ala Gly Gly Ala
    130                 135                 140

Thr Pro Lys Lys Ser Ala Lys Lys Thr Pro Lys Lys Ala Lys Lys Pro
145                 150                 155                 160

Ala Ala Ala Thr Val Thr Lys Lys Val Ala Lys Ser Pro Lys Lys Ala
                165                 170                 175

Lys Val Ala Lys Pro Lys Ala Ala Lys Ser Ala Ala Lys Ala Val
            180                 185                 190

Lys Pro Lys Ala Ala Lys Pro Lys Val Val Lys Pro Lys Lys Ala Ala
            195                 200                 205

Pro Lys Lys Lys
    210
```

(2) INFORMATION FOR SEQ ID NO:2:

(i) SEQUENCE CHARACTERISTICS:
      (A) LENGTH: 220 amino acids
      (B) TYPE: amino acid
      (D) TOPOLOGY: linear (ix) FEATURE:

(A) NAME/KEY: Peptide
        (B) LOCATION: 1..220
        (D) OTHER INFORMATION: /note= "product = Human Histone
            H1-S-2"

(xi) SEQUENCE DESCRIPTION: SEQ ID NO:2:

Ser Glu Thr Ala Pro Leu Ala Pro Thr Ile Pro Ala Pro Ala Glu Lys
1               5                   10                  15

Thr Pro Val Lys Lys Ala Lys Lys Ala Gly Ala Thr Ala Gly Lys
            20              25                  30

Arg Lys Ala Ser Gly Pro Pro Val Ser Glu Leu Ile Thr Lys Ala Val
            35              40                  45

Ala Ala Ser Lys Glu Arg Ser Gly Val Ser Leu Ala Ala Leu Lys Lys
50                      55                  60

Ala Leu Ala Ala Gly Tyr Asp Val Glu Lys Asn Asn Ser Arg Ile
65                  70              75                  80

Lys Leu Gly Leu Lys Ser Leu Val Ser Lys Gly Thr Leu Val Gln Thr
                85              90                  95

Lys Gly Thr Gly Ala Ser Gly Ser Phe Lys Leu Asn Lys Lys Ala Ala
                100             105                 110

Ser Gly Glu Gly Lys Pro Lys Ala Lys Ala Gly Ala Ala Lys Pro
            115             120                 125

Arg Lys Pro Ala Gly Ala Ala Lys Lys Pro Lys Lys Val Ala Gly Ala
            130             135                 140

Ala Thr Pro Lys Lys Ser Ile Lys Lys Thr Pro Lys Lys Val Lys Lys
145                 150             155                 160

Pro Ala Thr Ala Ala Gly Thr Lys Lys Val Ala Lys Ser Ala Lys Lys
                165             170                 175

Val Lys Thr Pro Gln Pro Lys Lys Ala Ala Lys Ser Pro Ala Lys Ala
                180             185                 190

Lys Ala Pro Lys Pro Lys Ala Ala Lys Pro Lys Ser Gly Lys Pro Lys
            195             200             205

Val Thr Lys Ala Lys Lys Ala Ala Pro Lys Lys Lys
            210             215                 220

(2) INFORMATION FOR SEQ ID NO:3:

(i) SEQUENCE CHARACTERISTICS:
        (A) LENGTH: 222 amino acids
        (B) TYPE: amino acid
        (D) TOPOLOGY: linear (ix) FEATURE:
        (A) NAME/KEY: Peptide
        (B) LOCATION: 1..222
        (D) OTHER INFORMATION: /note= "product = Human Histone
            H1-S-3"

(xi) SEQUENCE DESCRIPTION: SEQ ID NO:3:

Ser Glu Thr Ala Pro Ala Glu Thr Ala Thr Pro Ala Pro Val Glu Lys
1               5                   10                  15

Ser Pro Ala Lys Lys Lys Ala Thr Lys Ala Ala Gly Ala Gly Ala
            20              25                  30

Ala Lys Arg Lys Ala Thr Gly Pro Pro Val Ser Glu Leu Ile Thr Lys
            35              40                  45

Ala Val Ala Ala Ser Lys Glu Arg Asn Gly Leu Ser Leu Ala Ala Leu
50                      55                  60

Lys Lys Ala Leu Ala Ala Gly Gly Tyr Asp Val Glu Lys Asn Asn Ser
65                  70              75                  80

```
        Arg Ile Lys Leu Gly Leu Lys Ser Leu Val Ser Lys Gly Thr Leu Val
                         85                  90                  95

Gln Thr Lys Gly Thr Gly Ala Ser Gly Ser Phe Lys Leu Asn Lys Lys
                    100                 105                 110

Ala Ala Ser Gly Glu Ala Lys Pro Lys Ala Lys Lys Ala Gly Ala Ala
                    115                 120                 125

Lys Ala Lys Lys Pro Ala Gly Ala Thr Pro Lys Lys Ala Lys Lys Ala
                    130                 135                 140

Ala Gly Ala Lys Lys Ala Val Lys Lys Thr Pro Lys Lys Ala Lys Lys
        145                 150                 155                 160

Pro Ala Ala Ala Gly Val Lys Val Ala Lys Ser Pro Lys Lys Ala
                            165                 170                 175

Lys Ala Ala Lys Pro Lys Lys Ala Thr Lys Ser Pro Ala Lys Pro
                    180                 185                 190

Lys Ala Val Lys Pro Lys Ala Ala Lys Pro Lys Ala Ala Lys Pro Lys
                    195                 200                 205

Ala Ala Lys Pro Lys Ala Lys Lys Ala Ala Lys Lys Lys
        210                 215                 220
```

(2) INFORMATION FOR SEQ ID NO:4:

(i) SEQUENCE CHARACTERISTICS:
        (A) LENGTH: 218 amino acids
        (B) TYPE: amino acid
        (D) TOPOLOGY: linear (ix) FEATURE:
        (A) NAME/KEY: Peptide
        (B) LOCATION: 1..218
        (D) OTHER INFORMATION: /note= "product = Human Histone
            H1-S-4"

(xi) SEQUENCE DESCRIPTION: SEQ ID NO:4:

```
        Ser Glu Thr Ala Pro Ala Ala Pro Ala Ala Pro Ala Pro Ala Glu Lys
        1               5                   10                  15

Thr Pro Val Lys Lys Lys Ala Arg Lys Ser Ala Gly Ala Ala Lys Arg
                    20                  25                  30

Lys Ala Ser Gly Pro Pro Val Ser Glu Leu Ile Thr Lys Ala Val Ala
                    35                  40                  45

Ala Ser Lys Glu Arg Ser Gly Val Ser Leu Ala Ala Leu Lys Lys Ala
                    50                  55                  60

Leu Ala Ala Ala Gly Tyr Asp Val Glu Lys Asn Asn Ser Arg Ile Lys
        65                  70                  75                  80

Leu Gly Leu Lys Ser Leu Val Ser Lys Gly Thr Leu Val Gln Thr Lys
                            85                  90                  95

Gly Thr Gly Ala Ser Gly Ser Phe Lys Leu Asn Lys Lys Ala Ala Ser
                    100                 105                 110

Gly Glu Ala Lys Pro Lys Ala Lys Lys Ala Gly Ala Ala Lys Ala Lys
                    115                 120                 125

Lys Pro Ala Gly Ala Ala Lys Pro Lys Lys Ala Thr Gly Ala Ala
                    130                 135                 140

Thr Pro Lys Lys Ser Ala Lys Lys Thr Pro Lys Lys Ala Lys Lys Pro
        145                 150                 155                 160

Ala Ala Ala Ala Gly Ala Lys Lys Ala Lys Ser Pro Lys Lys Ala Lys
                            165                 170                 175

Ala Ala Lys Pro Lys Lys Ala Pro Lys Ser Pro Ala Lys Ala Lys Ala
                    180                 185                 190
```

```
        Val Lys Pro Lys Ala Ala Lys Pro Lys Thr Ala Lys Pro Lys Ala Ala
                    195                 200                 205

Lys Pro Lys Lys Ala Ala Lys Lys Lys
                    210                 215

(2) INFORMATION FOR SEQ ID NO:5:

(i) SEQUENCE CHARACTERISTICS:
        (A) LENGTH: 193 amino acids
        (B) TYPE: amino acid
        (D) TOPOLOGY: linear (ix) FEATURE:
        (A) NAME/KEY: Peptide
        (B) LOCATION: 1..193
        (D) OTHER INFORMATION: /note= "product = Human Histone
            H1-o"

(xi) SEQUENCE DESCRIPTION: SEQ ID NO:5:

Thr Glu Asn Ser Thr Ser Ala Pro Ala Ala Lys Pro Lys Arg Ala Lys
    1               5                   10                  15

Ala Ser Lys Lys Ser Thr Asp His Pro Lys Tyr Ser Asp Met Ile Val
                    20                  25                  30

Ala Ala Ile Gln Ala Glu Lys Asn Arg Ala Gly Ser Ser Arg Gln Ser
                35                  40                  45

Ile Gln Lys Tyr Ile Lys Ser His Tyr Lys Val Gly Glu Asn Ala Asp
    50                  55                  60

Ser Gln Ile Lys Leu Ser Ile Lys Arg Leu Val Thr Thr Gly Val Leu
    65                  70                  75                  80

Lys Gln Thr Lys Gly Val Gly Ala Ser Gly Ser Phe Arg Leu Ala Lys
                    85                  90                  95

Ser Asp Glu Pro Lys Lys Ser Val Ala Phe Lys Lys Thr Lys Lys Glu
                    100                 105                 110

Ile Lys Lys Val Ala Thr Pro Lys Lys Ala Ser Lys Pro Lys Lys Ala
                    115                 120                 125

Ala Ser Lys Ala Pro Thr Lys Lys Pro Lys Ala Thr Pro Val Lys Lys
                130                 135                 140

Ala Lys Lys Lys Leu Ala Ala Thr Pro Lys Lys Ala Lys Lys Pro Lys
    145                 150                 155                 160

Thr Val Lys Ala Lys Pro Val Lys Ala Ser Lys Pro Lys Lys Ala Lys
                    165                 170                 175

Pro Val Lys Pro Lys Ala Lys Ser Ser Ala Lys Arg Ala Gly Lys Lys
                    180                 185                 190

Lys (2) INFORMATION FOR SEQ ID NO:6:

(i) SEQUENCE CHARACTERISTICS:
        (A) LENGTH: 206 amino acids
        (B) TYPE: amino acid
        (D) TOPOLOGY: linear (ix) FEATURE:
        (A) NAME/KEY: Peptide
        (B) LOCATION: 1..206
        (D) OTHER INFORMATION: /note= "product = Human Histone
            H1t"

(xi) SEQUENCE DESCRIPTION: SEQ ID NO:6:

Ser Glu Thr Val Pro Ala Ala Ser Ala Ser Ala Gly Val Ala Ala Met
    1               5                   10                  15
```

```
Glu Lys Leu Pro Thr Lys Lys Arg Gly Arg Lys Pro Ala Gly Leu Ile
             20                  25                  30

Ser Ala Ser Arg Lys Val Pro Asn Leu Ser Val Ser Lys Leu Ile Thr
         35                  40                  45

Glu Ala Leu Ser Val Ser Gln Glu Arg Val Gly Met Ser Leu Val Ala
     50                  55                  60

Leu Lys Lys Ala Leu Ala Ala Gly Tyr Asp Val Glu Lys Asn Asn
 65                  70                  75                  80

Ser Arg Ile Lys Leu Ser Leu Lys Ser Leu Val Asn Lys Gly Ile Leu
                 85                  90                  95

Val Gln Thr Arg Gly Thr Gly Ala Ser Gly Ser Phe Lys Leu Ser Lys
             100                 105                 110

Lys Val Ile Pro Lys Ser Thr Arg Ser Lys Ala Lys Lys Ser Val Ser
             115                 120                 125

Ala Lys Thr Lys Lys Leu Val Leu Ser Arg Asp Ser Lys Ser Pro Lys
 130                 135                 140

Thr Ala Lys Thr Asn Lys Arg Ala Lys Lys Pro Arg Ala Thr Thr Pro
145                 150                 155                 160

Lys Thr Val Arg Ser Gly Arg Lys Ala Lys Gly Ala Lys Gly Lys Gln
                 165                 170                 175

Lys Gln Lys Ser Pro Val Lys Ala Arg Ala Ser Lys Ser Lys Leu Thr
             180                 185                 190

Gln His His Glu Val Asn Val Arg Lys Ala Thr Ser Lys Lys
         195                 200                 205

(2) INFORMATION FOR SEQ ID NO:7:

(i) SEQUENCE CHARACTERISTICS:
        (A) LENGTH: 35 amino acids
        (B) TYPE: amino acid
        (D) TOPOLOGY: linear (xi) SEQUENCE DESCRIPTION: SEQ ID NO:7:

Ser Glu Thr Ala Pro Ala Glu Thr Ala Thr Pro Ala Pro Val Glu Lys
 1               5                  10                  15

Ser Pro Ala Lys Lys Lys Ala Thr Lys Lys Ala Ala Gly Ala Gly Ala
             20                  25                  30

Ala Lys Arg
         35

(2) INFORMATION FOR SEQ ID NO:8:

(i) SEQUENCE CHARACTERISTICS:
        (A) LENGTH: 699 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..699

(ix) FEATURE:
        (A) NAME/KEY: misc_feature
        (B) LOCATION: 1..699
        (D) OTHER INFORMATION: /note= "product = NANUC-2 heavy
            chain"

(xi) SEQUENCE DESCRIPTION: SEQ ID NO:8:

GCC CAG GTG AAA CTG CTC GAG CAG TCT GGG GGA GGC GTG GTC CAG CCT    48
Ala Gln Val Lys Leu Leu Glu Gln Ser Gly Gly Gly Val Val Gln Pro
```

```
                1               5                   10                  15
          GGG AAG TCC CTG AGA CTC TCC TGT GCA GCC TCT GGA TTC ACC TTC AGG      96
          Gly Lys Ser Leu Arg Leu Ser Cys Ala Ala Ser Gly Phe Thr Phe Arg
                           20                  25                  30

AAC TAT GGC ATG CAC TGG GTC CGG CAG GCT CCA GGC AAG GGG CTG GAG     144
          Asn Tyr Gly Met His Trp Val Arg Gln Ala Pro Gly Lys Gly Leu Glu
                       35                  40                  45

TGG GTG GCA GGT ATT TCC TCT GAT GGA AGA AAA AAA AAG TAT GTA GAC     192
          Trp Val Ala Gly Ile Ser Ser Asp Gly Arg Lys Lys Lys Tyr Val Asp
                   50                  55                  60

TCC GTG AAG GGC CGA TTC ACC ATC TCC AGA GAC AAG TCC AAG AAC ACG     240
          Ser Val Lys Gly Arg Phe Thr Ile Ser Arg Asp Lys Ser Lys Asn Thr
           65                  70                  75                  80

CTG TAT CTG CAA ATG AAC AGC CTC AGA GCT GAG GAC ACG GCT GTG TAT     288
          Leu Tyr Leu Gln Met Asn Ser Leu Arg Ala Glu Asp Thr Ala Val Tyr
                           85                  90                  95

TAC TGT GCG AAA TTG TCC CGC GCG GGT GGT TTT GAC ATC TGG GGC CAA     336
          Tyr Cys Ala Lys Leu Ser Arg Ala Gly Gly Phe Asp Ile Trp Gly Gln
                       100                 105                 110

GGG ACA ATG GTC ACC GTC TCT TCA GCC TCC ACC AAG GGC CCA TCG GTC     384
          Gly Thr Met Val Thr Val Ser Ser Ala Ser Thr Lys Gly Pro Ser Val
                   115                 120                 125

TTT CCC CTG GCA CCC TCC TCC AAG AGC ACC TCT GGG GGC ACA GCG GCC     432
          Phe Pro Leu Ala Pro Ser Ser Lys Ser Thr Ser Gly Gly Thr Ala Ala
           130                 135                 140

CTG GGC TGC CTG GTC AAG GAC TAC TTC CCC GAA CCG GTG ACG GTG TCG     480
          Leu Gly Cys Leu Val Lys Asp Tyr Phe Pro Glu Pro Val Thr Val Ser
          145                 150                 155                 160

TGG AAC TCA GGC GCC CTG ACC AGC GGC GTG CAC ACC TTC CCG GCT GTC     528
          Trp Asn Ser Gly Ala Leu Thr Ser Gly Val His Thr Phe Pro Ala Val
                           165                 170                 175

CTA CAG TCC TCA GGA CTC TAC TCC CTC AGC AGC GTG GTG ACC GTG CCC     576
          Leu Gln Ser Ser Gly Leu Tyr Ser Leu Ser Ser Val Val Thr Val Pro
                       180                 185                 190

TCC AGC AGC TTG GGC ACC CAG ACC TAC ATC TGC AAC GTG AAT CAC AAG     624
          Ser Ser Ser Leu Gly Thr Gln Thr Tyr Ile Cys Asn Val Asn His Lys
                   195                 200                 205

CCC AGC AAC ACC AAG GTG GAC AAG AAA GCA GAG CCC AAA TCT TGT GAC     672
          Pro Ser Asn Thr Lys Val Asp Lys Lys Ala Glu Pro Lys Ser Cys Asp
           210                 215                 220

AAA ACT AGT CAC CAC CAC CAC CAC CAC                                 699
          Lys Thr Ser His His His His His His
          225                 230
```

(2) INFORMATION FOR SEQ ID NO:9:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:9:

```
Ala Gln Val Lys Leu Leu Glu Gln Ser Gly Gly Gly Val Val Gln Pro
 1               5                   10                  15

Gly Lys Ser Leu Arg Leu Ser Cys Ala Ala Ser Gly Phe Thr Phe Arg
                 20                  25                  30

Asn Tyr Gly Met His Trp Val Arg Gln Ala Pro Gly Lys Gly Leu Glu
             35                  40                  45
```

```
Trp Val Ala Gly Ile Ser Ser Asp Gly Arg Lys Lys Tyr Val Asp
     50                  55                  60

Ser Val Lys Gly Arg Phe Thr Ile Ser Arg Asp Lys Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Lys Leu Ser Arg Ala Gly Gly Phe Asp Ile Trp Gly Gln
            100                 105                 110

Gly Thr Met Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Ala Glu Pro Lys Ser Cys Asp
    210                 215                 220

Lys Thr Ser His His His His His His
225                 230
```

(2) INFORMATION FOR SEQ ID NO:10:

(i) SEQUENCE CHARACTERISTICS:
        (A) LENGTH: 642 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..642

(ix) FEATURE:
        (A) NAME/KEY: misc_feature
        (B) LOCATION: 1..642
        (D) OTHER INFORMATION: /note= "product = NANUC-2 light chain"

(xi) SEQUENCE DESCRIPTION: SEQ ID NO:10:

```
GCC GAG CTC ACG CAG TCT CCA GGC ACC CTG TCT TTG TTT CCA GGG GAA      48
Ala Glu Leu Thr Gln Ser Pro Gly Thr Leu Ser Leu Phe Pro Gly Glu
 1               5                  10                  15

AGA GCC ACT CTC TCC TGC AGG GCC AGT CAG AGA ATT AGC ACC AGT TTC      96
Arg Ala Thr Leu Ser Cys Arg Ala Ser Gln Arg Ile Ser Thr Ser Phe
             20                  25                  30

TTA GCC TGG TAC CAG CAG AAG CCT GGC CAG TCT CCC AGG CTC CTC ATC     144
Leu Ala Trp Tyr Gln Gln Lys Pro Gly Gln Ser Pro Arg Leu Leu Ile
         35                  40                  45

TTT GAT GCA TCC ACC AGG GCC CCT GGC ATC CCT GAC AGG TTC AGT GCC     192
Phe Asp Ala Ser Thr Arg Ala Pro Gly Ile Pro Asp Arg Phe Ser Ala
     50                  55                  60

AGT TGG TCT GGG ACA GAC TTC ACT CTC ACC ATC AGC AGA CTG GAG CCT     240
Ser Trp Ser Gly Thr Asp Phe Thr Leu Thr Ile Ser Arg Leu Glu Pro
 65                  70                  75                  80

GAA GAT TTT GCA GTC TAT TAC TGT CAA CAT TAT GGT GGG TCT CCC TGG     288
Glu Asp Phe Ala Val Tyr Tyr Cys Gln His Tyr Gly Gly Ser Pro Trp
```

```
                    85                       90                       95
ACG TTC GGC CAA GGG ACC AAG GTG GAA ATC AAG CGA ACT GTG GCT GCA           336
Thr Phe Gly Gln Gly Thr Lys Val Glu Ile Lys Arg Thr Val Ala Ala
            100                     105                     110

CCA TCT GTC TTC ATC TTC CCG CCA TCT GAT GAG CAG TTG AAA TCT GGA           384
Pro Ser Val Phe Ile Phe Pro Pro Ser Asp Glu Gln Leu Lys Ser Gly
        115                     120                     125

ACT GCC TCT GTT GTG TGC CTG CTG AAT AAC TTC TAT CCC AGA GAG GCC           432
Thr Ala Ser Val Val Cys Leu Leu Asn Asn Phe Tyr Pro Arg Glu Ala
130                     135                     140

AAA GTA CAG TGG AAG GTG GAT AAC GCC CTC CAA TCG GGT AAC TCC CAG           480
Lys Val Gln Trp Lys Val Asp Asn Ala Leu Gln Ser Gly Asn Ser Gln
145                     150                     155                 160

GAG AGT GTC ACA GAG CAG GAC AGC AAG GAC AGC ACC TAC AGC CTC AGC           528
Glu Ser Val Thr Glu Gln Asp Ser Lys Asp Ser Thr Tyr Ser Leu Ser
                165                     170                     175

AGC ACC CTG ACG CTG AGC AAA GCA GAC TAC GAG AAA CAC AAA GTC TAC           576
Ser Thr Leu Thr Leu Ser Lys Ala Asp Tyr Glu Lys His Lys Val Tyr
            180                     185                     190

GCC TGC GAA GTC ACC CAT CAG GGC CTG AGC TCG CCC GTC ACA AAG AGC           624
Ala Cys Glu Val Thr His Gln Gly Leu Ser Ser Pro Val Thr Lys Ser
        195                     200                     205

TTC AAC AGG GGA GAG TGT                                                    642
Phe Asn Arg Gly Glu Cys
    210

(2) INFORMATION FOR SEQ ID NO:11:

(i) SEQUENCE CHARACTERISTICS:
        (A) LENGTH: 214 amino acids
        (B) TYPE: amino acid
        (D) TOPOLOGY: linear (ii) MOLECULE TYPE: protein (xi) SEQUENCE DESCRIPTION: SEQ ID NO:11:

Ala Glu Leu Thr Gln Ser Pro Gly Thr Leu Ser Leu Phe Pro Gly Glu
  1               5                  10                  15

Arg Ala Thr Leu Ser Cys Arg Ala Ser Gln Arg Ile Ser Thr Ser Phe
                 20                  25                  30

Leu Ala Trp Tyr Gln Gln Lys Pro Gly Gln Ser Pro Arg Leu Leu Ile
             35                  40                  45

Phe Asp Ala Ser Thr Arg Ala Pro Gly Ile Pro Asp Arg Phe Ser Ala
         50                  55                  60

Ser Trp Ser Gly Thr Asp Phe Thr Leu Thr Ile Ser Arg Leu Glu Pro
 65                  70                  75                  80

Glu Asp Phe Ala Val Tyr Tyr Cys Gln His Tyr Gly Gly Ser Pro Trp
                 85                  90                  95

Thr Phe Gly Gln Gly Thr Lys Val Glu Ile Lys Arg Thr Val Ala Ala
            100                     105                     110

Pro Ser Val Phe Ile Phe Pro Pro Ser Asp Glu Gln Leu Lys Ser Gly
        115                     120                     125

Thr Ala Ser Val Val Cys Leu Leu Asn Asn Phe Tyr Pro Arg Glu Ala
130                     135                     140

Lys Val Gln Trp Lys Val Asp Asn Ala Leu Gln Ser Gly Asn Ser Gln
145                     150                     155                 160

Glu Ser Val Thr Glu Gln Asp Ser Lys Asp Ser Thr Tyr Ser Leu Ser
                165                     170                     175
```

-continued

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

(2) INFORMATION FOR SEQ ID NO:12:

(i) SEQUENCE CHARACTERISTICS:
        (A) LENGTH: 73 amino acids
        (B) TYPE: amino acid
        (D) TOPOLOGY: linear (xi) SEQUENCE DESCRIPTION: SEQ ID NO:12:

```
Ser Glu Thr Ala Pro Leu Ala Pro Thr Ile Pro Ala Pro Ala Glu Lys
1               5                   10                  15

Thr Pro Val Lys Lys Ala Lys Ala Gly Ala Thr Ala Gly Lys
            20                  25                  30

Arg Lys Ala Ser Gly Pro Pro Val Ser Glu Leu Ile Thr Lys Ala Val
            35                  40                  45

Ala Ala Ser Lys Glu Arg Ser Gly Val Ser Leu Ala Ala Leu Lys Lys
            50                  55                  60

Ala Leu Ala Ala Ala Gly Tyr Asp Val
65                  70
```

(2) INFORMATION FOR SEQ ID NO:13:

(i) SEQUENCE CHARACTERISTICS:
        (A) LENGTH: 147 amino acids
        (B) TYPE: amino acid
        (D) TOPOLOGY: linear (xi) SEQUENCE DESCRIPTION: SEQ ID NO:13:

```
Glu Lys Asn Asn Ser Arg Ile Lys Leu Gly Leu Lys Ser Leu Val Ser
1               5                   10                  15

Lys Gly Thr Leu Val Gln Thr Lys Gly Thr Gly Ala Ser Gly Ser Phe
            20                  25                  30

Lys Leu Asn Lys Lys Ala Ala Ser Gly Glu Gly Lys Pro Lys Ala Lys
            35                  40                  45

Lys Ala Gly Ala Ala Lys Pro Arg Lys Pro Ala Gly Ala Ala Lys Lys
            50                  55                  60

Pro Lys Lys Val Ala Gly Ala Ala Thr Pro Lys Lys Ser Ile Lys Lys
65                  70                  75                  80

Thr Pro Lys Lys Val Lys Pro Ala Thr Ala Ala Gly Thr Lys Lys
                85                  90                  95

Val Ala Lys Ser Ala Lys Lys Val Lys Thr Pro Gln Pro Lys Lys Ala
                100                 105                 110

Ala Lys Ser Pro Ala Lys Ala Lys Ala Pro Lys Pro Lys Ala Ala Lys
            115                 120                 125

Pro Lys Ser Gly Lys Pro Lys Val Thr Lys Ala Lys Ala Ala Pro
            130                 135                 140

Lys Lys Lys
145
```

(2) INFORMATION FOR SEQ ID NO:14:

(i) SEQUENCE CHARACTERISTICS:
        (A) LENGTH: 113 amino acids

```
          (B) TYPE: amino acid
          (D) TOPOLOGY: linear (xi) SEQUENCE DESCRIPTION: SEQ ID NO:14:

Asn Lys Lys Ala Ala Ser Gly Glu Gly Lys Pro Lys Ala Lys Lys Ala
  1               5                   10                  15

Gly Ala Ala Lys Pro Arg Lys Pro Ala Gly Ala Ala Lys Lys Pro Lys
                  20                  25                  30

Lys Val Ala Gly Ala Ala Thr Pro Lys Lys Ser Ile Lys Lys Thr Pro
              35                  40                  45

Lys Lys Val Lys Lys Pro Ala Thr Ala Ala Gly Thr Lys Lys Val Ala
          50                  55                  60

Lys Ser Ala Lys Lys Val Lys Thr Pro Gln Pro Lys Lys Ala Ala Lys
  65                  70                  75                  80

Ser Pro Ala Lys Ala Lys Ala Pro Lys Pro Lys Ala Ala Lys Pro Lys
                  85                  90                  95

Ser Gly Lys Pro Lys Val Thr Lys Ala Lys Lys Ala Ala Pro Lys Lys
                  100                 105                 110

Lys (2) INFORMATION FOR SEQ ID NO:15:

(i) SEQUENCE CHARACTERISTICS:
          (A) LENGTH: 15 amino acids
          (B) TYPE: amino acid
          (D) TOPOLOGY: linear (xi) SEQUENCE DESCRIPTION: SEQ ID NO:15:

Phe Lys Leu Asn Lys Lys Ala Ala Ser Gly Glu Ala Lys Pro Lys
  1               5                   10                  15

(2) INFORMATION FOR SEQ ID NO:16:

(i) SEQUENCE CHARACTERISTICS:
          (A) LENGTH: 15 amino acids
          (B) TYPE: amino acid
          (D) TOPOLOGY: linear (xi) SEQUENCE DESCRIPTION: SEQ ID NO:16:

Glu Ala Lys Pro Lys Val Lys Lys Ala Gly Gly Thr Lys Pro Lys
  1               5                   10                  15

(2) INFORMATION FOR SEQ ID NO:17:

(i) SEQUENCE CHARACTERISTICS:
          (A) LENGTH: 15 amino acids
          (B) TYPE: amino acid
          (D) TOPOLOGY: linear (xi) SEQUENCE DESCRIPTION: SEQ ID NO:17:

Gly Thr Lys Pro Lys Lys Pro Val Gly Ala Ala Lys Lys Pro Lys
  1               5                   10                  15

(2) INFORMATION FOR SEQ ID NO:18:

(i) SEQUENCE CHARACTERISTICS:
          (A) LENGTH: 15 amino acids
          (B) TYPE: amino acid
          (D) TOPOLOGY: linear (xi) SEQUENCE DESCRIPTION: SEQ ID NO:18:

Ala Lys Lys Pro Lys Lys Ala Ala Gly Gly Ala Thr Pro Lys Lys
  1               5                   10                  15
```

(2) INFORMATION FOR SEQ ID NO:19:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:19:

```
Ala Thr Pro Lys Lys Ser Ala Lys Lys Thr Pro Lys Lys Ala Lys
1               5                  10                  15
```

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:20:

```
Pro Lys Lys Ala Lys Lys Pro Ala Ala Ala Thr Val Thr Lys Lys
1               5                  10                  15
```

(2) INFORMATION FOR SEQ ID NO:21:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:21:

```
Thr Val Thr Lys Lys Val Ala Lys Ser Pro Lys Lys Ala Lys Val
1               5                  10                  15
```

(2) INFORMATION FOR SEQ ID NO:22:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:22:

```
Lys Lys Ala Lys Val Ala Lys Pro Lys Lys Ala Ala Lys Ser Ala
1               5                  10                  15
```

(2) INFORMATION FOR SEQ ID NO:23:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:23:

```
Ala Ala Lys Ser Ala Ala Lys Ala Val Lys Pro Lys Ala Ala Lys
1               5                  10                  15
```

(2) INFORMATION FOR SEQ ID NO:24:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:24:

```
Pro Lys Ala Ala Lys Pro Lys Val Val Lys Pro Lys Lys Ala Ala
1               5                  10                  15
```

-continued (2) INFORMATION FOR SEQ ID NO:25:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:25:

```
Lys Pro Lys Val Val Lys Pro Lys Lys Ala Ala Pro Lys Lys Lys
1               5                   10                  15
```

(2) INFORMATION FOR SEQ ID NO:26:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:26:

```
Lys Pro Ala Ala Ala
1               5
```